(12) United States Patent
Koch et al.

(10) Patent No.: US 11,617,604 B2
(45) Date of Patent: Apr. 4, 2023

(54) INTRAMEDULLARY NAIL ASSEMBLY

(71) Applicant: DEPUY SYNTHES PRODUCTS, INC., Raynham, MA (US)

(72) Inventors: Roger Koch, Aarau (CH); Walter Widmer, Oberdorf (CH); Heinz Zbinden, Bettlach (CH); Mark Allemann, Rumisberg (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 16/849,009

(22) Filed: Apr. 15, 2020

(65) Prior Publication Data

US 2021/0322070 A1 Oct. 21, 2021

(51) Int. Cl.
*A61B 17/72* (2006.01)
*A61B 17/00* (2006.01)

(52) U.S. Cl.
CPC ...... *A61B 17/7241* (2013.01); *A61B 17/7283* (2013.01); *A61B 2017/00526* (2013.01); *A61B 2017/00862* (2013.01)

(58) Field of Classification Search
CPC .......................................... A61B 17/72–7291
See application file for complete search history.

(56) References Cited

U.S. PATENT DOCUMENTS

| | | | |
|---|---|---|---|
| 5,484,438 A | 1/1996 | Pennig | |
| 5,653,709 A | 8/1997 | Frigg | |
| 6,228,086 B1 | 5/2001 | Wahl et al. | |
| 6,296,645 B1 | 10/2001 | Hover et al. | |
| 6,569,165 B2 | 5/2003 | Wahl et al. | |
| 6,652,528 B2 | 11/2003 | Vandewalle | |
| 6,709,436 B1 | 3/2004 | Hover et al. | |
| 6,783,529 B2 | 8/2004 | Hover et al. | |
| 6,786,908 B2 | 9/2004 | Hover et al. | |
| 6,808,527 B2 | 10/2004 | Lower et al. | |
| 6,921,400 B2 | 7/2005 | Sohngen | |
| 6,926,719 B2 | 8/2005 | Sohngen et al. | |
| 6,932,819 B2 | 8/2005 | Wahl et al. | |
| 7,763,021 B2 | 7/2010 | Cole et al. | |
| 8,066,706 B2 | 11/2011 | Schlienger et al. | |
| 8,109,930 B2 | 2/2012 | Schlienger et al. | |

(Continued)

FOREIGN PATENT DOCUMENTS

| | | |
|---|---|---|
| CA | 2571494 A1 | 1/2006 |
| CA | 2571508 C | 3/2012 |

(Continued)

*Primary Examiner* — Eduardo C Robert
*Assistant Examiner* — Michelle C Eckman
(74) *Attorney, Agent, or Firm* — BakerHostetler

(57) ABSTRACT

An intramedullary nail assembly includes a body and an inlay. The body has an outer surface and an opposing inner surface. The outer surface extends from a leading end of the body to a trailing end of the body. The inner surface defines a cannulation that extends into the trailing end towards the leading end. The body comprises a leading body portion that defines the leading end, and a trailing body portion that defines the trailing end. The inlay is positionable within the cannulation of at least one of the leading body portion and the trailing body portion. The inlay includes an engagement member configured to engage the body to removably lock the inlay within the cannulation of the body.

15 Claims, 19 Drawing Sheets

(56) References Cited

U.S. PATENT DOCUMENTS

| | | |
|---|---|---|
| 8,303,590 B2 | 11/2012 | Elghazaly et al. |
| 8,414,582 B2 | 4/2013 | Overes et al. |
| 8,435,239 B2 | 5/2013 | Lutz et al. |
| 8,460,294 B2 | 6/2013 | Overes |
| 8,465,489 B2 | 6/2013 | Schlienger et al. |
| 8,771,271 B2 | 7/2014 | Overes |
| 8,888,779 B2 | 11/2014 | Senn et al. |
| 8,915,917 B2 | 12/2014 | Doherty et al. |
| 9,050,149 B2 | 6/2015 | LeCronier et al. |
| 9,095,440 B2 | 8/2015 | Orbay et al. |
| 9,237,909 B2 | 1/2016 | Schlienger et al. |
| 9,737,347 B2 | 8/2017 | Schlienger et al. |
| 2002/0103488 A1* | 8/2002 | Lower .................. A61B 17/72 606/62 |
| 2002/0151898 A1* | 10/2002 | Sohngen ............ A61B 17/7233 606/62 |
| 2002/0173792 A1 | 11/2002 | Severns et al. |
| 2003/0195515 A1 | 10/2003 | Sohngen |
| 2007/0270854 A1 | 11/2007 | Li et al. |
| 2008/0221577 A1 | 9/2008 | Elghazaly |
| 2008/0294164 A1 | 11/2008 | Frank et al. |
| 2010/0249781 A1* | 9/2010 | Haidukewych .... A61B 17/7241 606/62 |
| 2012/0109127 A1* | 5/2012 | Overes .................. A61L 27/34 606/64 |
| 2012/0157997 A1* | 6/2012 | Sohngen ............. A61B 17/744 606/64 |
| 2014/0296853 A1 | 10/2014 | Wolter |
| 2014/0296854 A1 | 10/2014 | Wolter |
| 2015/0272636 A1* | 10/2015 | Schwammberger ........ A61B 17/7241 606/62 |
| 2020/0323568 A1* | 10/2020 | Daly .................. A61B 17/7225 |

FOREIGN PATENT DOCUMENTS

| | | |
|---|---|---|
| CA | 2571508 A1 | 5/2012 |
| DE | 102010048052 A1 | 4/2012 |
| DE | 102010048052 B4 | 6/2015 |
| EP | 0306709 A2 | 3/1989 |
| EP | 2590583 A1 | 5/2013 |
| EP | 2590583 B1 | 2/2015 |
| JP | 2007236568 A | 9/2007 |
| WO | 2004100810 A1 | 11/2004 |
| WO | 2010014694 A1 | 2/2010 |
| WO | 2011018778 A1 | 2/2011 |
| WO | 2013134387 A1 | 9/2013 |
| WO | 2014096077 A1 | 6/2014 |
| WO | 2015144131 A1 | 10/2015 |
| WO | 2015172842 A1 | 11/2015 |

* cited by examiner

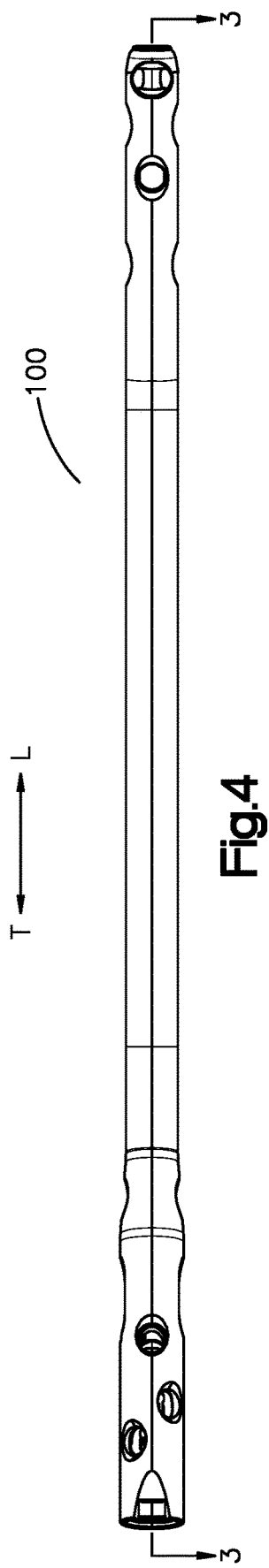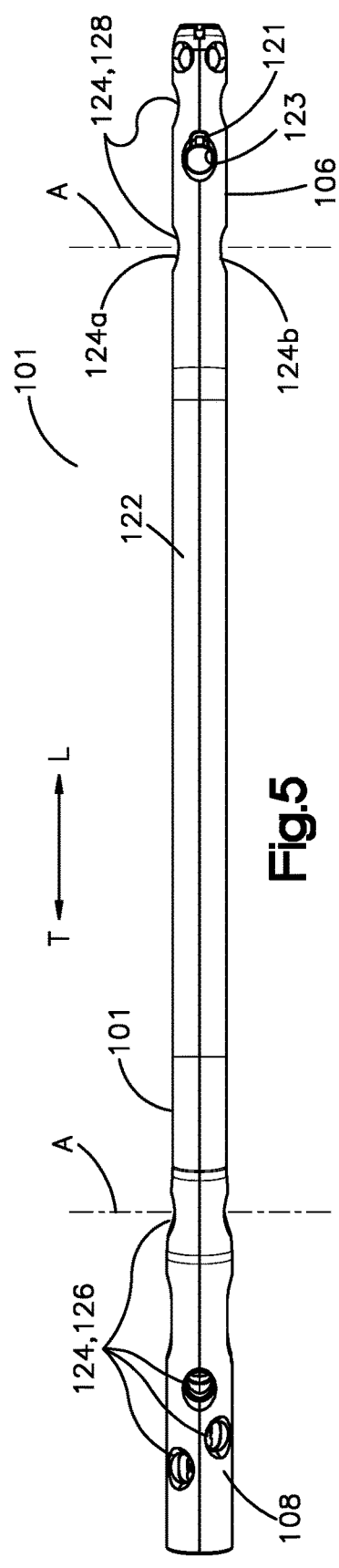

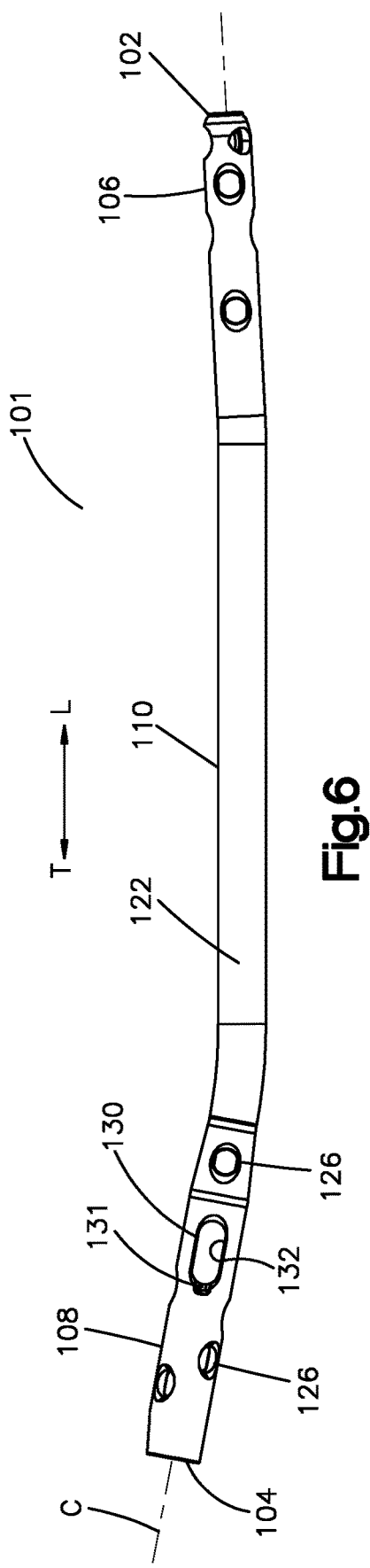
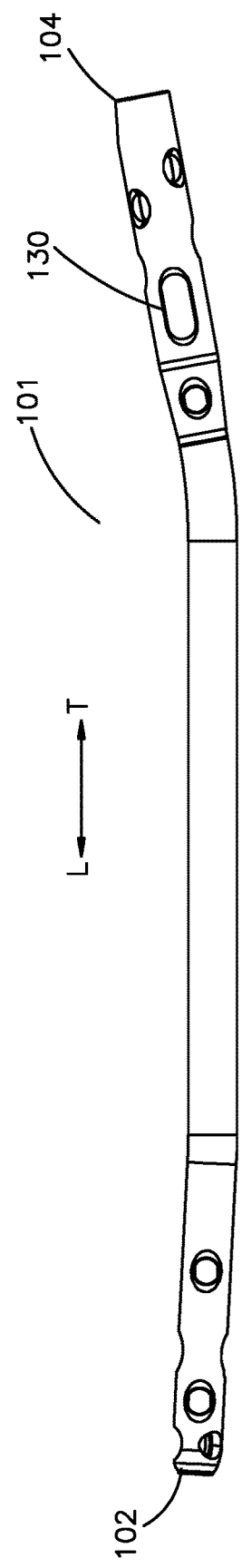

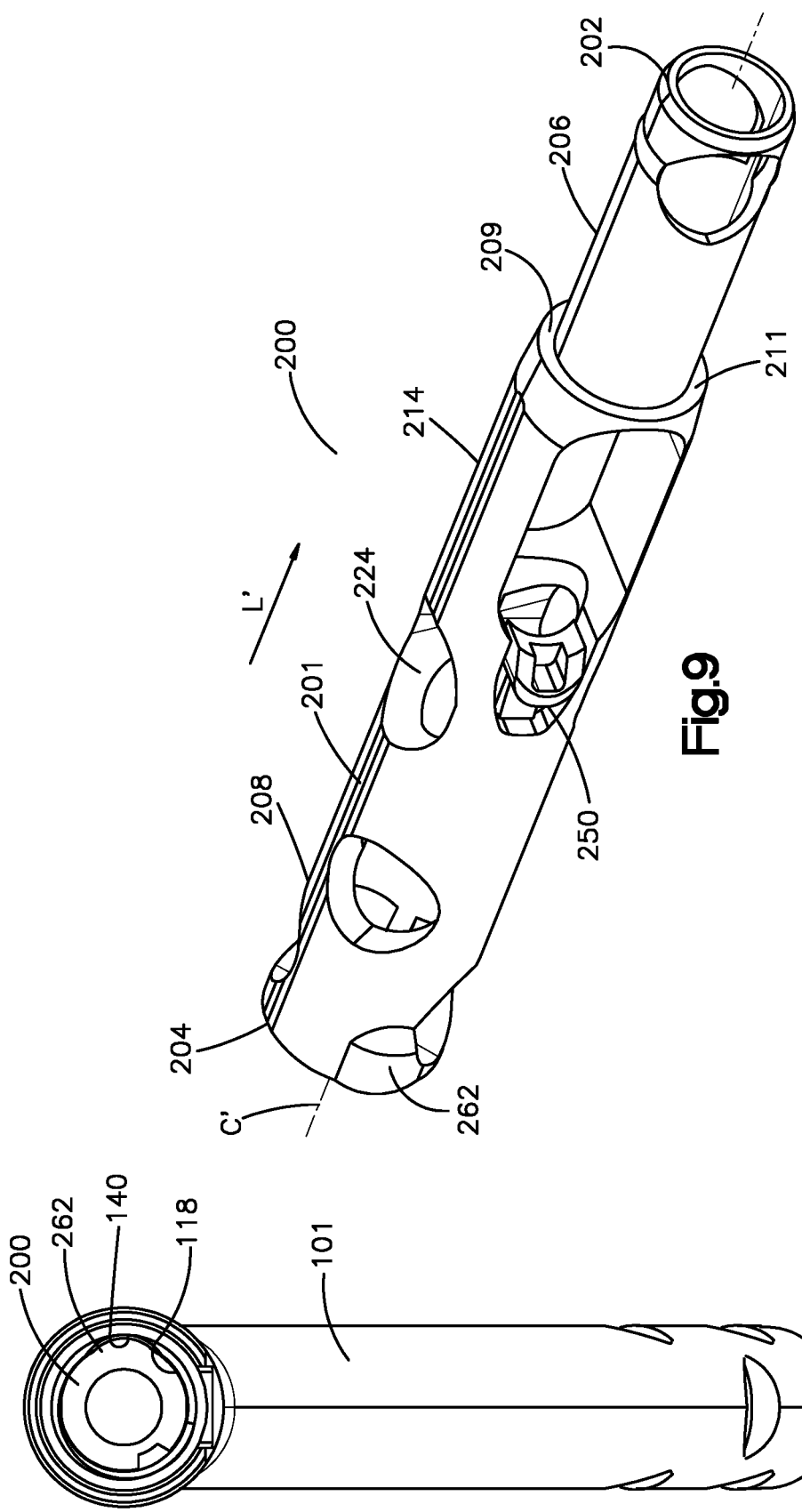

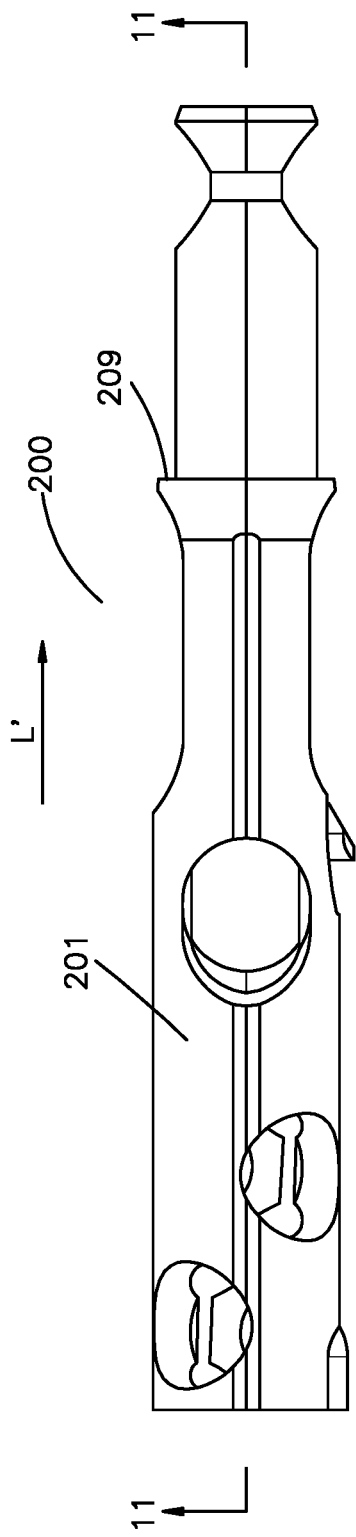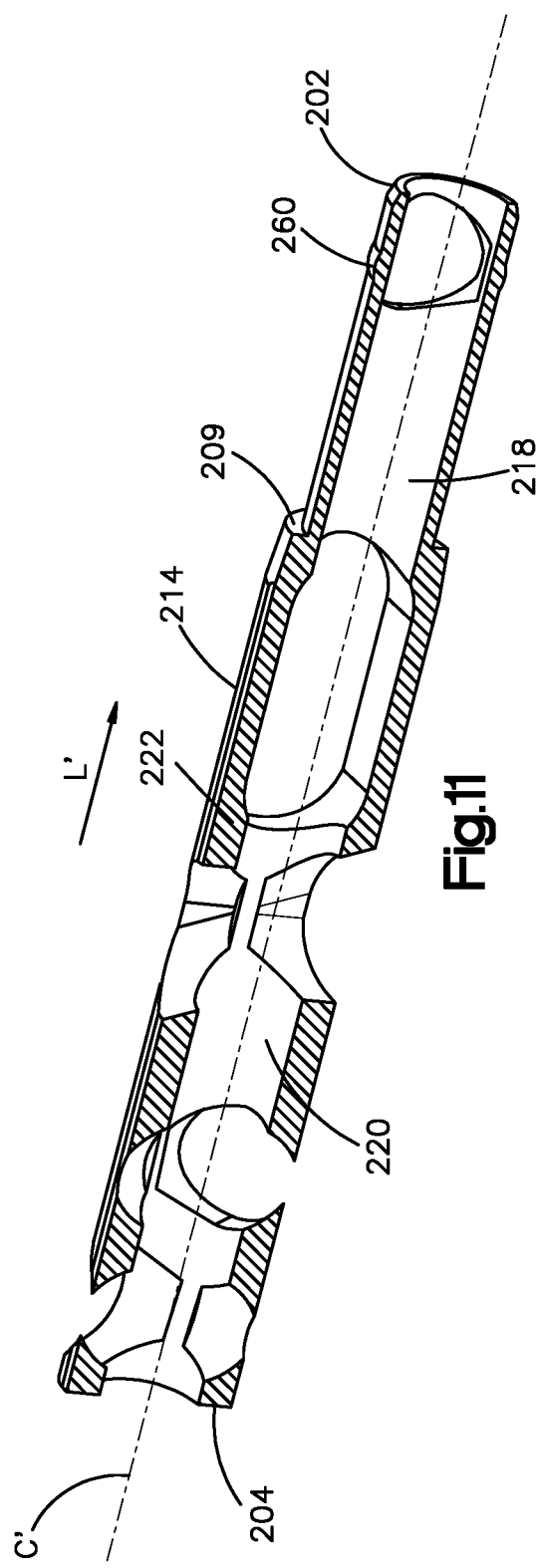

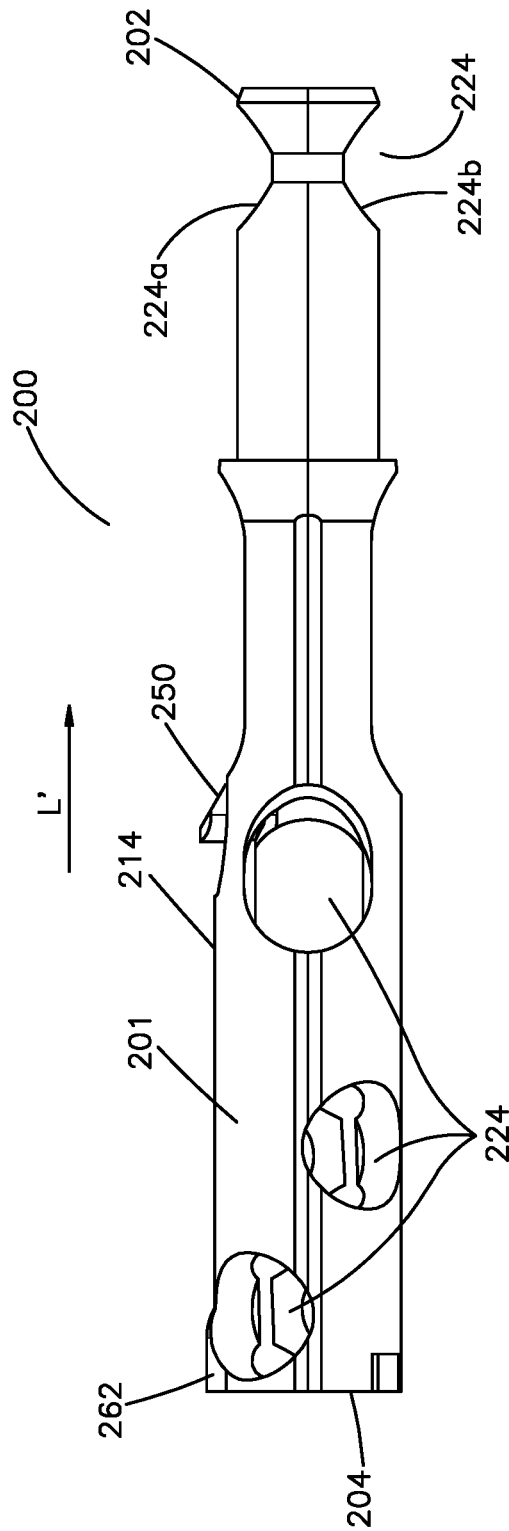

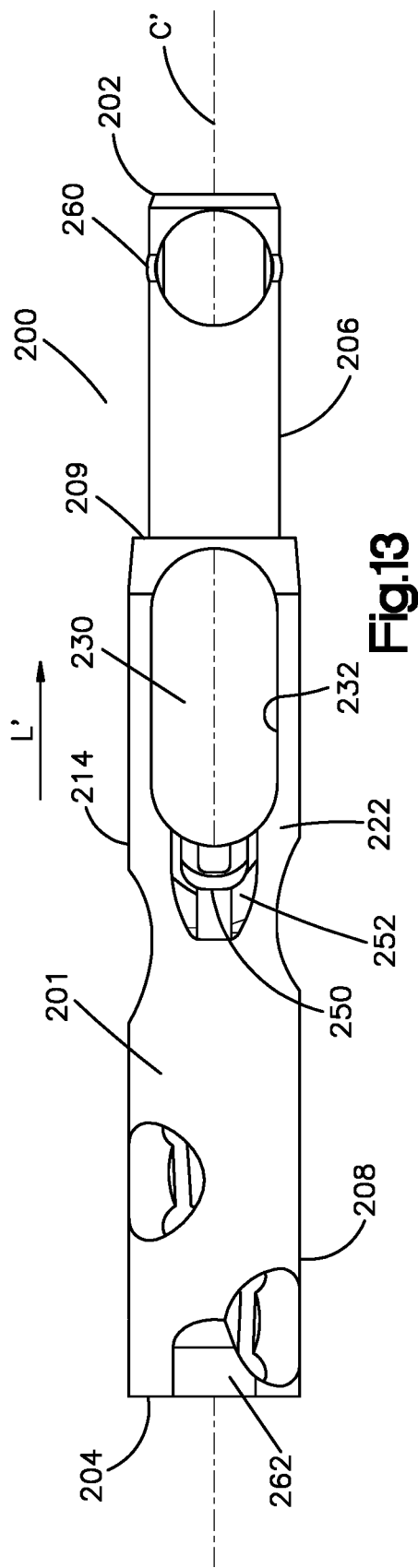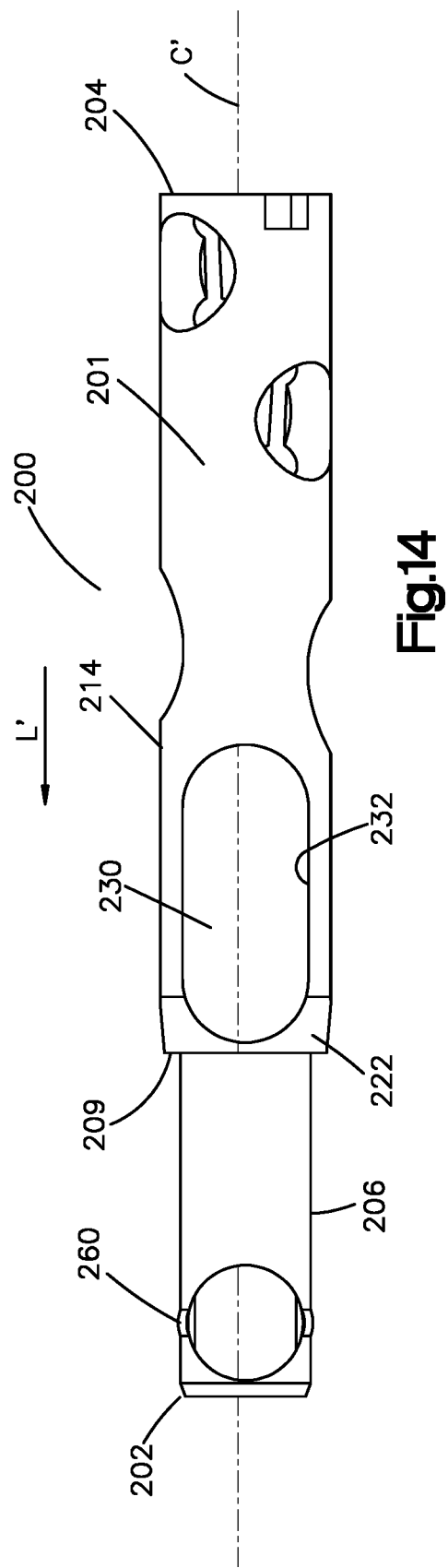

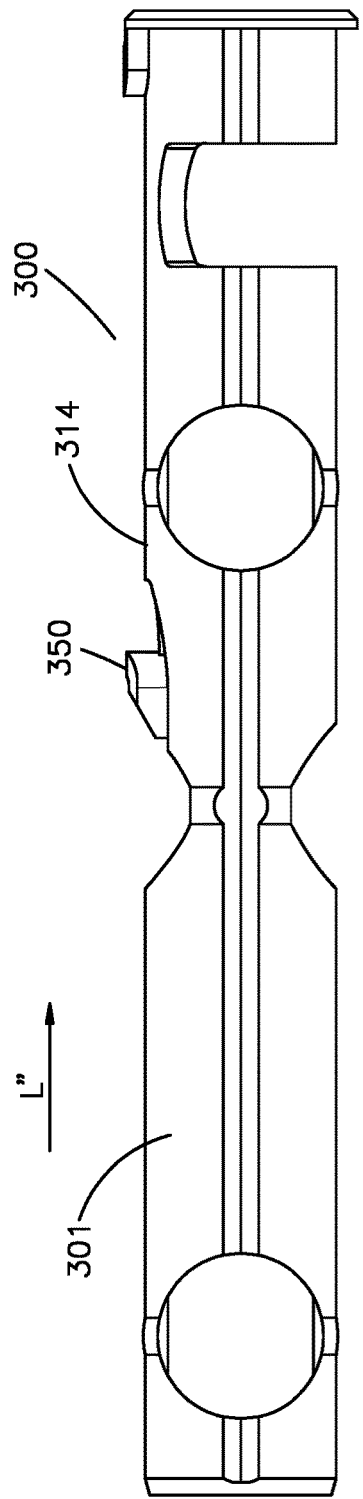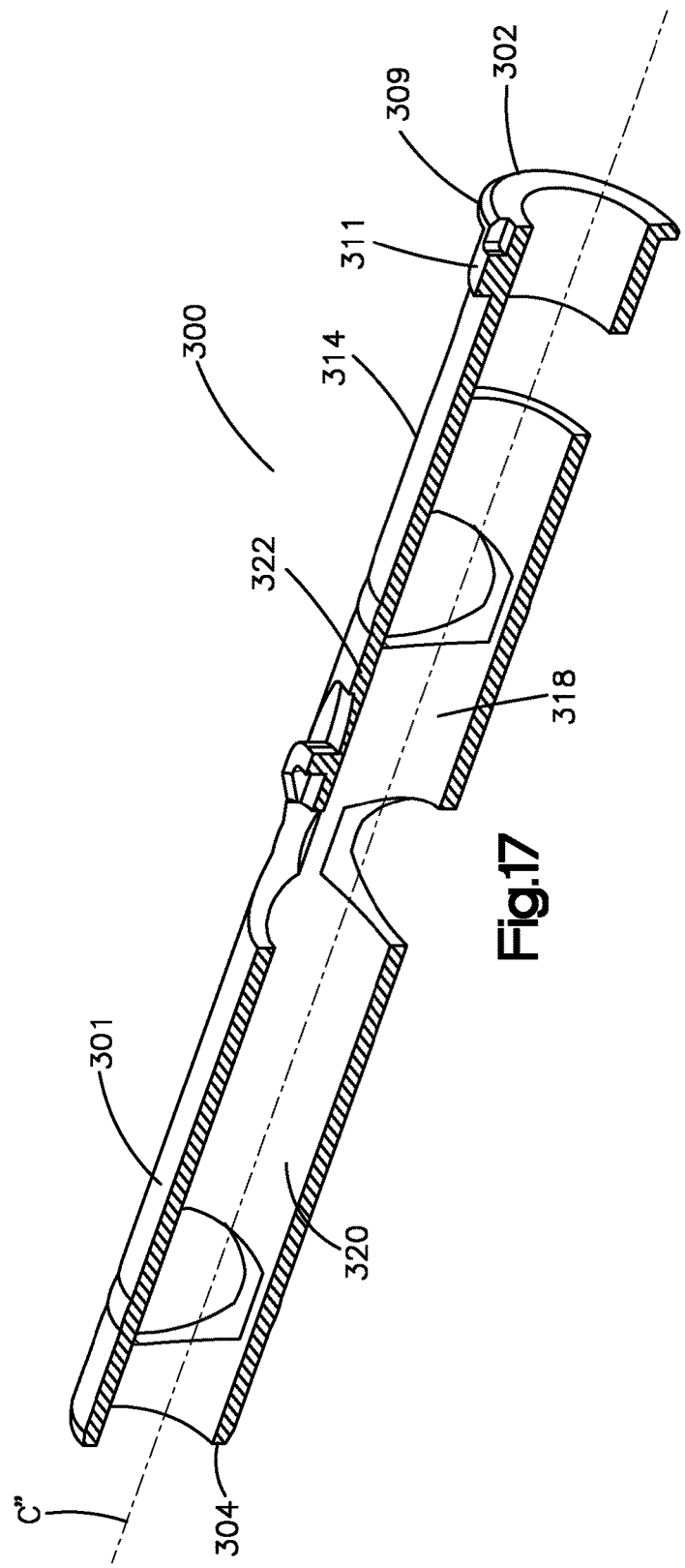

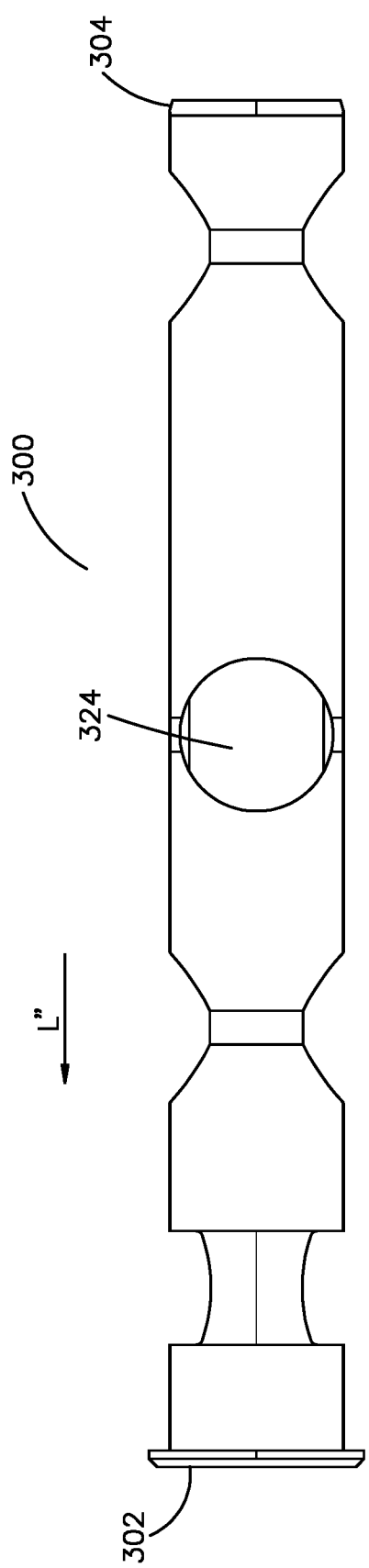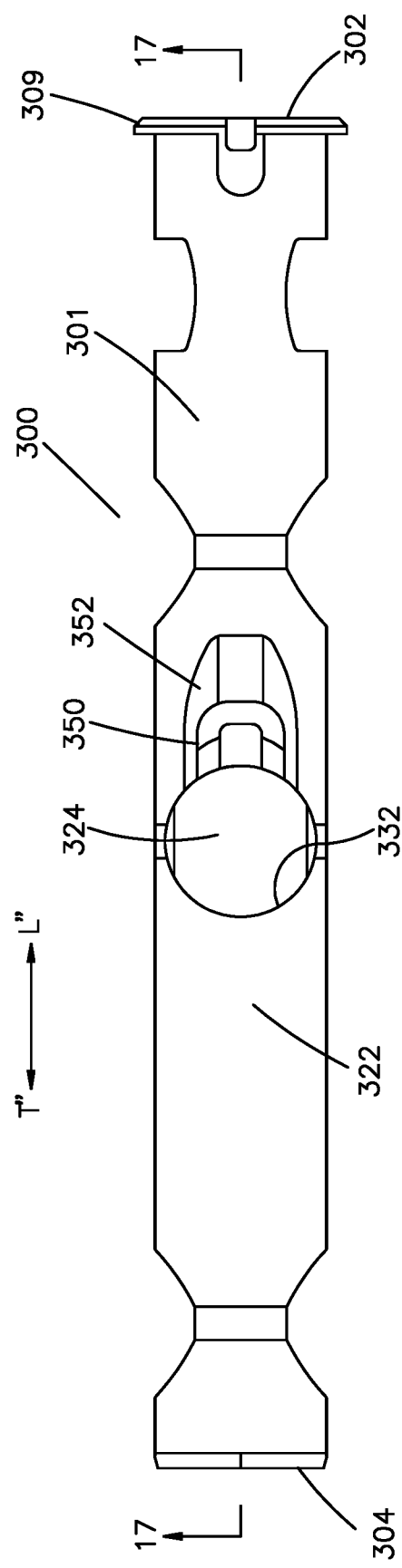

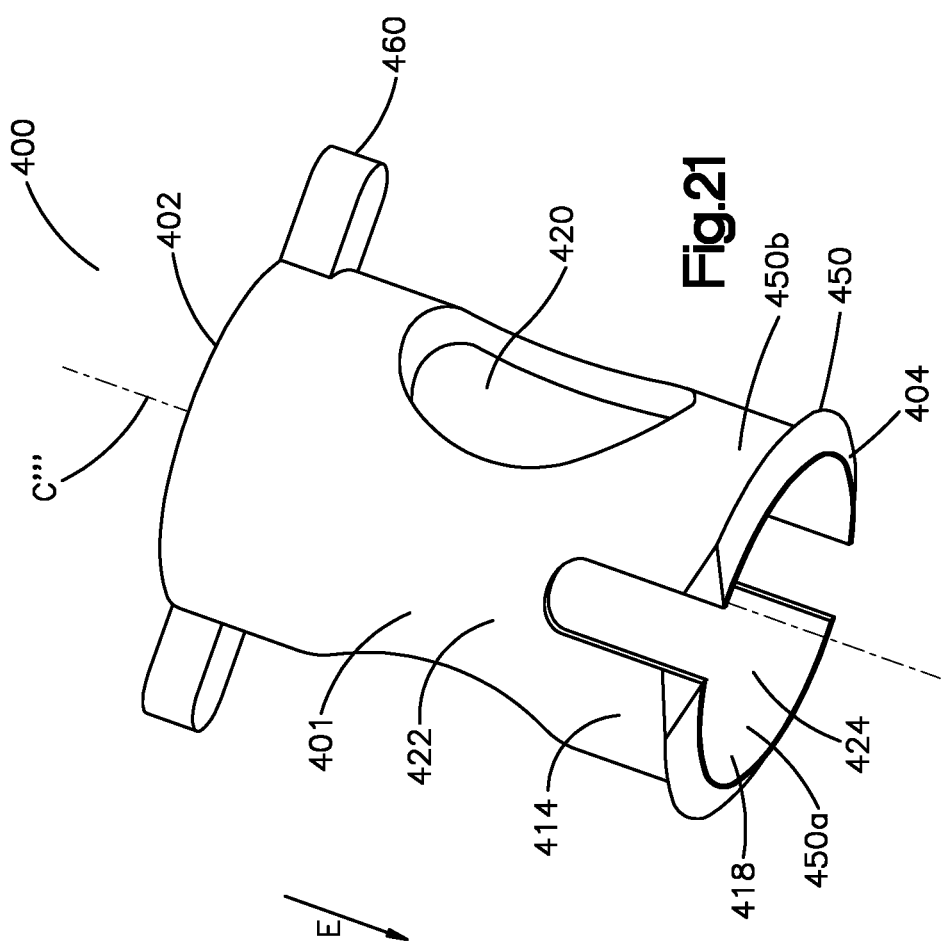

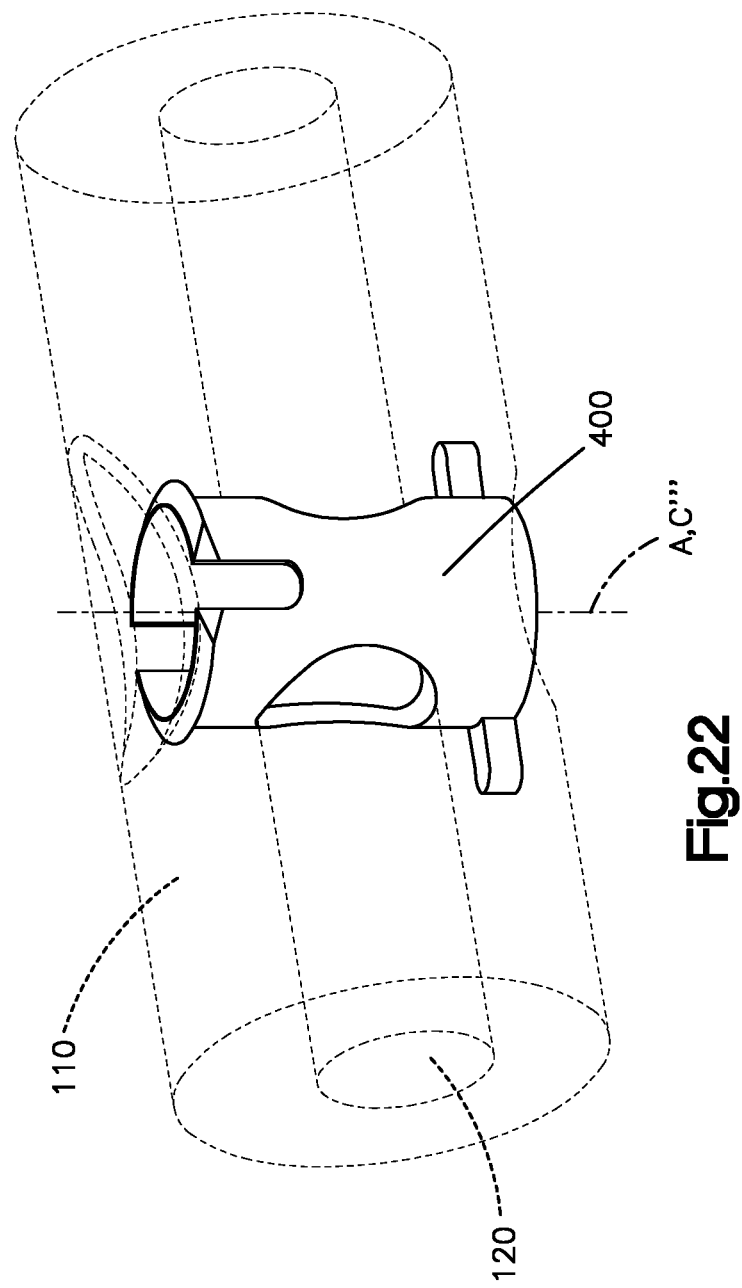

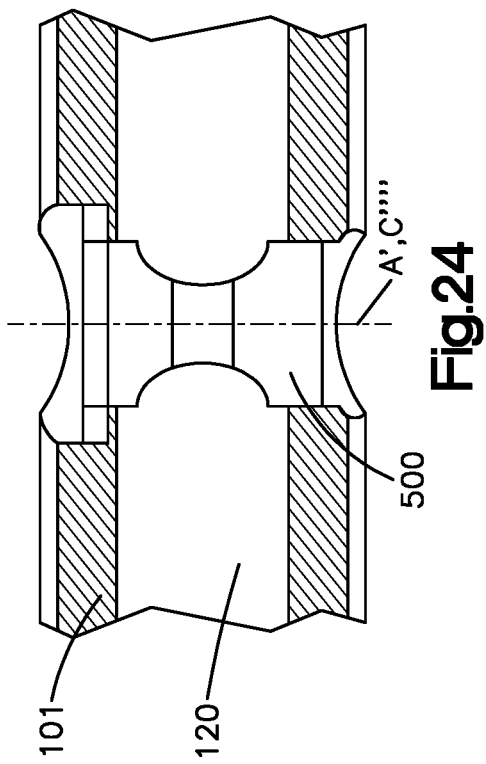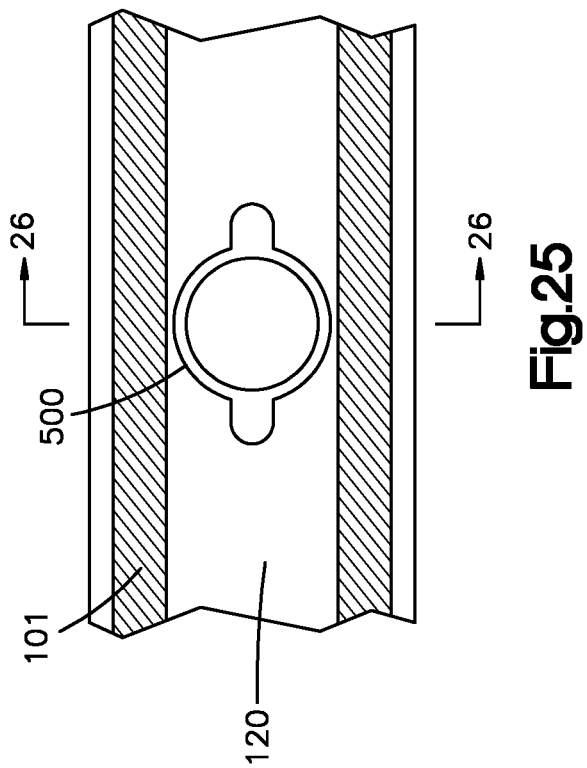

INTRAMEDULLARY NAIL ASSEMBLY

TECHNICAL FIELD

The present disclosure relates to systems, assemblies, and methods for the insertion and fixation of a nail into an intramedullary canal of a bone.

BACKGROUND

Intramedullary nails are commonly used to treat fractures in long bones of the body such as fractures in femurs, tibias, and humeri. To treat such fractures, the intramedullary nail is inserted into a medullary canal of the long bone such that the nail spans across one or more fractures to fragments of the long bone that are separated by the one or more fractures. Locking screws are then inserted through the bone and into the intramedullary nail perpendicular or with an oblique angle, thereby fixing the intramedullary nail to the bone. The intramedullary nail can remain in the medullary canal at least until the fracture is fused.

The foregoing background discussion is intended solely to aid the reader. It is not intended to limit the innovations described herein. Thus, the foregoing discussion should not be taken to indicate that any particular element of a prior system is unsuitable for use with the innovations described herein, nor is it intended to indicate that any element is essential in implementing the innovations described herein.

SUMMARY

The treatment of unstable tibia fractures is challenging. In recent years, the treatment of choice has been intramedullary nailing, due to the advantage of good mechanical stability, short time to union, and little soft tissue damage resulting in a shorter period of disability. In order to increase stability in distal fractures, the nail is typically locked with screws, but minor differences in the diameter of the screw hole and screw diameter compromise stability. Therefore, a new intramedullary nail system with angular stable distal and proximal screw fixation, as well as a screw pull-out safety function is desired.

An aspect of the present disclosure provides an intramedullary nail assembly. The intramedullary nail assembly comprises a body and an inlay. The body has an outer surface and an opposing inner surface. The outer surface extends from a leading end of the body to a trailing end of the body. The inner surface defining a cannulation that extends into the trailing end towards the leading end. The body comprises a leading body portion and a trailing body portion. The leading body portion defines the leading end of the body, and the trailing body portion is offset from the leading body portion along a trailing direction, and defines a trailing end of the body. The inlay is positionable within the cannulation of at least one of the leading body portion and the trailing body portion. The inlay includes an engagement member configured to engage the body to removably lock the inlay within the cannulation of the body.

Another aspect of the present disclosure provides an inlay for an intramedullary nail assembly. The intramedullary nail assembly includes a nail body having an outer surface and an opposing inner surface. The outer surface extends from a leading end of the nail body to a trailing end of the nail body. The inner surface defines a cannulation that extends into the trailing end towards the leading end. The inlay comprises an inlay body positionable within the cannulation of the nail body. The inlay body includes an engagement member configured to engage the nail body to removably lock the inlay within the cannulation of the nail body.

Another aspect of the present disclosure provides a method of manufacturing an intramedullary nail assembly. The method comprises: inserting a first inlay into the cannulation of the body within at least one of the leading body portion and the trailing body portion, the inlay including an engagement member configured to engage the body to removably lock the inlay within the cannulation of the body after the inlay is inserted. The method further comprises inserting a second inlay within the cannulation of the other of the leading body portion and the trailing body portion. The second inlay including a second engagement member configured to engage the body to removably lock the second inlay within the cannulation of the body after the second inlay is inserted.

This summary is provided to introduce a selection of concepts in a simplified form that are further described below in the Detailed Description section. This Summary is not intended to identify key features or essential features of the claimed subject matter, nor is it intended to be used to limit the scope of the claimed subject matter. Furthermore, the claimed subject matter is not constrained to limitations that solve any or all disadvantages noted in any part of this disclosure.

BRIEF DESCRIPTION OF THE DRAWINGS

The foregoing summary, as well as the following detailed description of illustrative embodiments of the present application, will be better understood when read in conjunction with the appended drawings. For the purposes of illustrating the present application, there are shown in the drawings illustrative embodiments of the disclosure. It should be understood, however, that the application is not limited to the precise arrangements and instrumentalities shown. In the drawings:

FIG. 4 illustrates an elevation view of a first side of the intramedullary nail shown in FIG. 2.

FIG. 5 illustrates an elevation view of a second side of the intramedullary nail shown in FIG. 2, opposite the first side.

FIG. 6 illustrates an elevation view of a third side of the intramedullary nail shown in FIG. 2, according to an aspect of this disclosure.

FIG. 7 illustrates an elevation view of a fourth side of the intramedullary nail shown in FIG. 6, opposite the third side.

FIG. 8 illustrates an end view of the intramedullary nail shown in FIG. 2, according to an aspect of this disclosure.

FIG. 9 illustrates a perspective view of a first inlay, according to an aspect of this disclosure.

FIG. 10 illustrates an elevation view of a first side of the first inlay shown in FIG. 9.

FIG. 11 illustrates a cross section of a perspective view of the first inlay shown in FIG. 9 taken along line 10-10.

FIG. 12 illustrates an elevation view of a second side of the first inlay shown in FIG. 10, opposite the first side.

FIG. 13 illustrates an elevation view of a third side of the first inlay shown in FIG. 9.

FIG. 14 illustrates an elevation view of a fourth side of the first inlay shown in FIG. 9.

FIG. 16 illustrates an elevation view of a first side of the second inlay shown in FIG. 15.

FIG. 17 illustrates a cross section of a perspective view of the second inlay shown in FIG. 15 taken along line 16-16.

FIG. 19 illustrates an elevation view of a third side of the second inlay shown in FIG. 15.

FIG. 20 illustrates an elevation view of a fourth side of the second inlay shown in FIG. 15.

FIG. 21 illustrates a perspective view of an alternative inlay design, according to an aspect of this disclosure.

FIG. 22 illustrates a perspective view of the alternative inlay shown in FIG. 21 positioned within a screw fixation hole of an intramedullary nail, according to an aspect of this disclosure.

FIGS. 24 and 25 illustrate a side view and a top view, respectively, of the inlay shown in FIG. 23 positioned within a bone-anchor fixation hole of an intramedullary nail, according to aspects of this disclosure.

DETAILED DESCRIPTION

Figure 1:
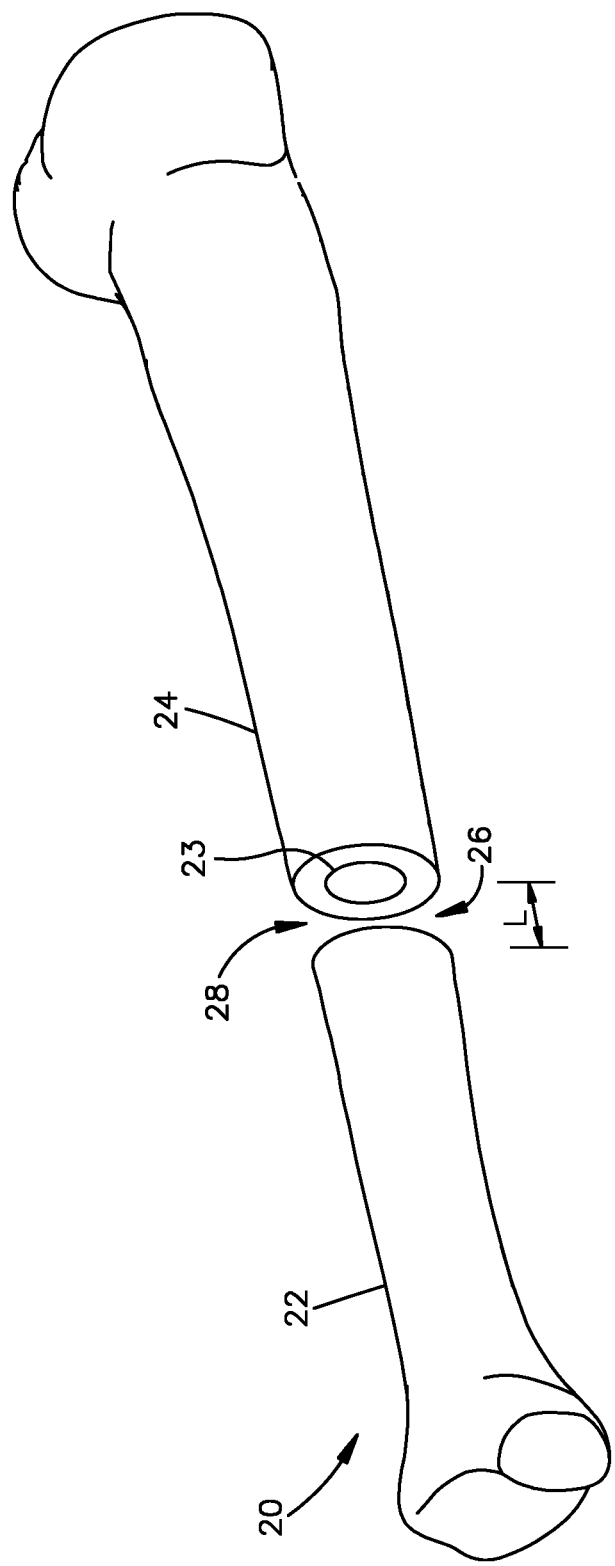
FIG. 1 illustrates a perspective view of a fractured long bone that defines a proximal bone segment and a distal bone segment separated from the proximal bone segment by a bone gap.

Certain terminology used in this description is for convenience only and is not limiting. The words "top", "bottom", "distal", "proximal", "leading", "trailing", "inner", "outer", "above", "below", "axial", "transverse", "circumferential," and "radial" designate directions in the drawings to which reference is made. The term "substantially" is intended to mean considerable in extent or largely but not necessarily wholly that which is specified. All ranges disclosed herein are inclusive of the recited endpoint and independently combinable (for example, the range of "from 2 grams to 10 grams" is inclusive of the endpoints, 2 grams and 10 grams, and all the intermediate values). The terminology includes the above-listed words, derivatives thereof and words of similar import.

FIG. 1 illustrates a long bone 20 that is elongate substantially along a longitudinal direction and is fractured so as to define a first or proximal bone segment 22 and a second distal bone segment 24 that is separated from the proximal bone segment 22 by a longitudinal bone gap 26 at a fracture location 28. It will be appreciated that the fractured long bone 20 can define a single fracture location 28 as illustrated, or can define multiple fracture locations that separate additional bone segments from each other at respective bone gaps. While the long bone 20 is a humerus in accordance with the illustrated aspect, the long bone 20 can be any long bone in the body that defines a medullary canal 23 suitable to receive an intramedullary nail so as to fix the proximal bone segment 22 to the distal bone segment 24. The bone gap 26 defines a bone gap distance D1 that extends along a longitudinal direction L and is greater than a desired distance suitable for reliable fixation of the proximal bone segment 22 to the distal bone segment 24. In an aspect, the intramedullary nail can include a compression feature that is configured to approximate the bone gap 26 to a distance that allows for reliable fixation of the bone segments 22 and 24 across the bone gap 26 during healing, although, in an alternative example, the intramedullary nail can be devoid of the compression feature.

Figure 2:
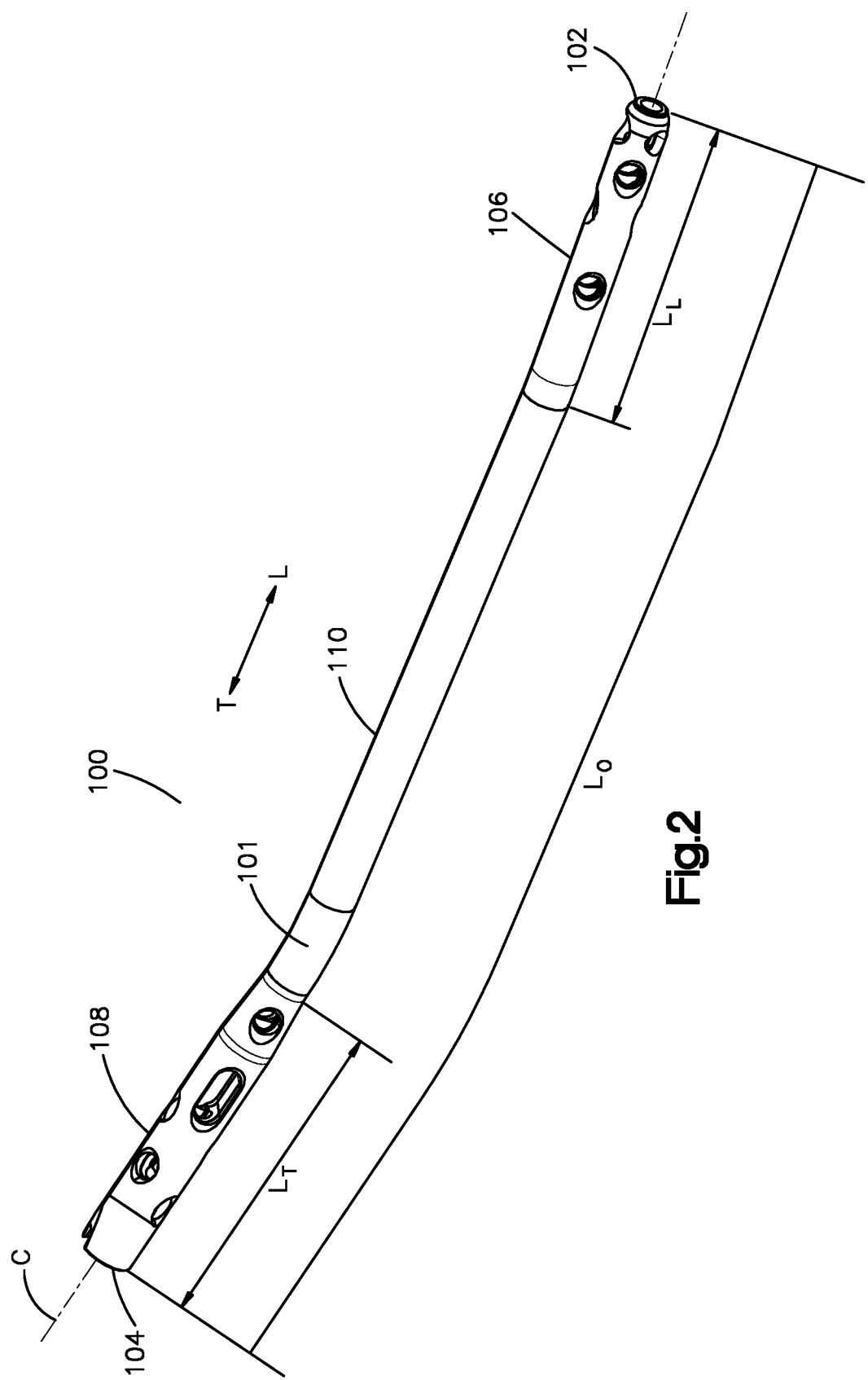
FIG. 2 illustrates a perspective view of an intramedullary nail assembly, according to an aspect of this disclosure.
Figure 3:
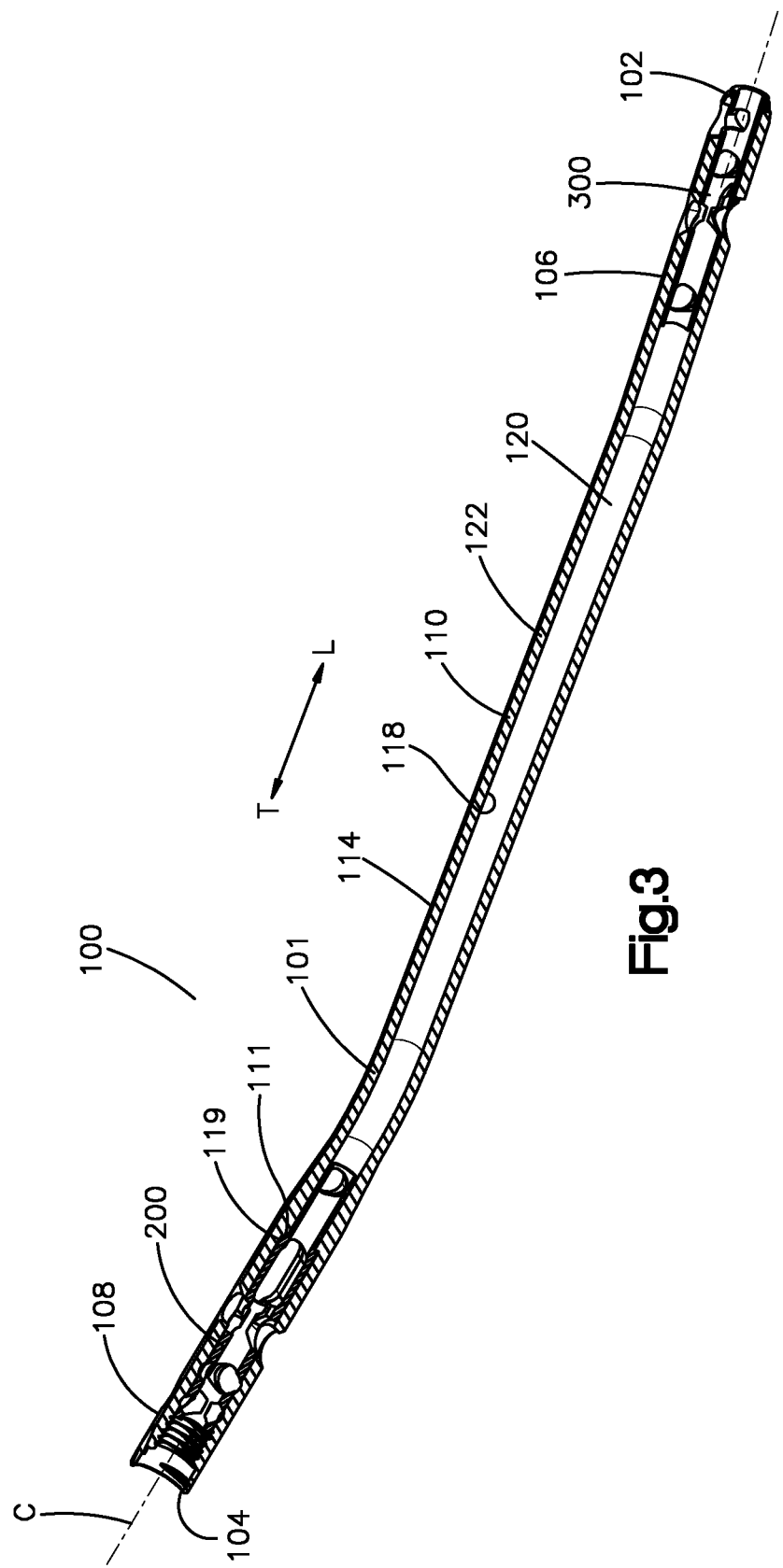
FIG. 3 illustrates a cross section of a perspective view of the intramedullary nail assembly shown in FIG. 2 taken along line 3-3 of FIG. 4.

FIGS. 2-4 illustrate a perspective view of an intramedullary nail assembly 100, a perspective view of a cross section of the intramedullary nail assembly 100, and an elevation view of a first side of the intramedullary nail assembly 100, respectively, according to aspects of this disclosure. The cross section of the intramedullary nail assembly 100 illustrated in FIG. 3 is taken along line 3-3 shown in FIG. 4. The intramedullary nail assembly 100 includes an intramedullary nail 101 (e.g. body), and can include one or both of a first inlay 200 and a second inlay 300. The intramedullary nail 101 is elongate from a first end 102 (e.g. insertion end or leading end) to a second end 104 (e.g. trailing end). The first end 102 can be considered to be a distal end, and can define a first terminal or outermost end of the intramedullary nail 101. The second end 104 can be considered to be a proximal end and can define a second terminal or outermost end of the intramedullary nail 101. As used herein, the term "proximal end" refers to an end that is closer to the medical professional during the medical procedure than the distal end, and the term "distal end" refers to an end that is further from the medical professional during the medical procedure than the proximal end. Further, the term "proximal direction" refers to a direction that extends towards the medical professional during the medical procedure, while the term "distal direction" refers to a direction that extends away from the medical professional during the medical procedure.

The intramedullary nail 101 is substantially elongate along a central pathway that extends from the trailing end 104 to the leading end 102. In at least some aspect, the central pathway can be defined by a central axis C of the intramedullary nail 101 that extends from the trailing end 104 to the leading end 102. It will be appreciated that the central pathway or central axis C of the intramedullary nail 101 can be straight or curved. Thus, the intramedullary nail 101 can be straight or curved as it extends along the central pathway or central axis C from the trailing end 104 to the leading end 102. The intramedullary nail 101 can be inserted into a medullary canal of a long bone such that the central pathway or central axis C extends along the length of the medullary canal.

The intramedullary nail 101 has a leading or distal body portion 106 and a trailing or proximal body portion 108 that are offset from one another. The intramedullary nail 101 also has an intermediate body portion 110 between the leading body portion 106 and the trailing body portion 108. The leading body portion 106 can extend from the leading end 102 of the intramedullary nail 101 towards the trailing end 104 along a trailing direction T, which can also be referred to as a proximal direction. Further, the trailing body portion 108 can extend from the trailing end 104 towards the leading end 102 along a leading direction L, which can also be referred to as an insertion or distal direction. For example, the leading body portion 106 can extend from the leading end 102 to the intermediate body portion 110, and the trailing body portion 108 can extend from the trailing end 104 to the intermediate body portion 110. It will be understood that the leading direction L extends from the trailing end 104 towards the leading end 106, and the trailing direction T extends in a direction opposite the leading direction L (e.g., from the leading end 102 towards the trailing end 104).

In an aspect, the trailing body portion 108 has a length $L_T$ that is less than half of an overall length $L_O$ of the intramedullary nail 101, such as less than or equal to one third of an overall length $L_O$ of the intramedullary nail 101, such as less than or equal to one quarter of the overall length $L_O$ of the intramedullary nail 101. Additionally, or alternatively, in at least some aspects, the leading body portion 106 has a length $L_L$ that is less than half of an overall length $L_O$ of the intramedullary nail 101, such as less than or equal to one third of an overall length $L_O$ of the intramedullary nail 101, such as less than or equal to one quarter of the overall length $L_O$ of the intramedullary nail 101.

The intramedullary nail 101 has an outer surface 114 that extends from the leading body portion 106 to the trailing body portion 108. The outer surface 114 can extend from the trailing end 104 to the leading end 102. The outer surface 114 can define an outer-most perimeter of the intramedullary nail 101. Further, the outer surface 114 can have any suitable cross-sectional shape as desired. For example, the outer surface 114 can be substantially circular in cross section along a plane that is substantially perpendicular to the central pathway or central axis C. Additionally, or alternatively, the intramedullary nail 101 can define a plurality of recesses that extend into the outer surface 114. The recesses can be spaced circumferentially from one another around an outer perimeter of the intramedullary nail 101 and can be elongate as they extend between the leading body portion 106 and the trailing body portion 108.

The intramedullary nail 101 has an inner surface 118 opposite the outer surface 114. Thus, the intramedullary nail 101 includes a tubular wall 122 between the inner surface 118 and the outer surface 114. The inner surface 118 defines a cannulation 120 that extends into the trailing end 104 in the leading direction L. The cannulation 120 can extend to the leading body portion 106. In an aspect, the cannulation 120 can extend through the leading end 102. Alternatively, the cannulation 120 can terminate prior to the leading end 102 such as in the leading body portion 106 or the intermediate body portion 110. The cannulation 120 can be configured (e.g., sized and shaped) so as to receive a rod, such as a reaming rod, therein as the intramedullary nail 101 is guided along the rod into the medullary canal of the bone. The cannulation 120 can extend along the central pathway or central axis C of the intramedullary nail 101. The inner surface 118 can have a plurality of cross-sections along the central pathway or central axis C, each cross-section defined in a plane that is perpendicular to the central pathway or central axis C. The inner surface 118 in each cross-section can have any suitable cross-sectional shape as desired. For example, the inner surface 118 in each cross-section can define a cross-sectional shape that is closed such as a circle, oval, square, rectangle, or other shape.

The inner surface 118 may further include a receiving or body shoulder 119. The receiving shoulder can be defined by a shoulder surface 111. The shoulder surface 111 may be angularly offset from, such as substantially perpendicular to, the central axis C. In alternative aspects, the shoulder surface 111 may have a conical shape, curved shape, or other shape. The shoulder surface 111 is configured to face in a direction toward the trailing end 104 such that a cross-sectional dimension (e.g. diameter) of the inner surface 118 located proximal to the shoulder surface 111 is greater than a cross-sectional dimension (e.g. diameter) of an innermost edge of the shoulder surface 111.

FIG. 5 illustrates an elevation view of a second side of the intramedullary nail assembly 100, according to an aspect of this disclosure. The intramedullary nail 101 defines a plurality of fastener holes 124 (e.g. bone anchor fixation holes). Each bone-anchor fixation hole 124 is configured to receive a fastener (e.g. bone anchor, screw, bolt, or other fastener) so as to attach the intramedullary nail 101 to a bone. The bone-anchor fixation holes 124 can include at least one trailing bone-anchor fixation hole 126 and at least one leading bone-anchor fixation hole 128. Each bone-anchor fixation hole 124 can intersect the cannulation 120. Each bone-anchor fixation hole 124 is configured to receive a bone anchor that extends through the bone-anchor fixation hole 124 so as to attach the intramedullary nail 101 to a bone. In particular, each bone-anchor fixation hole 124 can extend into the outer surface 114 and at least partially, such as entirely, through the intramedullary nail 101. For instance, each bone-anchor fixation hole 124 can extend into the outer surface 114 on a first side of the intramedullary nail 101 and out of the outer surface 114 on a second side of the intramedullary nail 101, opposite the first side. Thus, each bone-anchor fixation hole 124 can extend from an opening 124a on a first side of the intramedullary nail 101 to an opening 124b on the second side of the intramedullary nail 100. As such, each bone-anchor fixation hole 124 can be considered to be a through hole, although aspects of the disclosure are not limited to through holes. At least some of the bone-anchor fixation holes 124 can extend through the tubular wall 122 on a first side of the intramedullary nail 101 and through the tubular wall 122 on a second side of the intramedullary nail 101, opposite the first side.

Each bone-anchor fixation hole 124 extends through the intramedullary nail 101 along a central bone-anchor axis A that is angled with respect to the central axis C of the intramedullary nail 101. For example, the central axis C of the intramedullary nail 101 extends along a first direction adjacent each bone-anchor fixation hole 124, and each bone-anchor fixation hole 124 extends into the intramedullary nail 101 along the central bone-anchor axis A that extends along a second direction, the second direction forming a non-zero angle with the first direction. Each bone-anchor fixation hole 124 may extend through the intramedullary nail 101 along the central axis A that forms a non-zero angle, such as a right angle or an oblique angle, with the central axis C of the intramedullary nail 101. Each bone-anchor fixation hole 124 can be unthreaded or can include internal threading to receive external threading of a fastener (e.g. bone anchor, screw, bolt, or other fastener). Each of the bone-anchor fixation holes 124 may be preformed (e.g. pre-drilled) in the nail 101 following a core diameter of the bone anchor.

Each trailing bone-anchor fixation hole 126 and each leading bone-anchor fixation hole 128 may be positioned in the trailing body portion 108 and the leading body portion 106, respectively. It will be appreciated that the bone-anchor fixation holes 124 may be positioned in the intermediate body portion 110.

At least one trailing bone-anchor fixation hole 126 can have an axis A that is aligned along the longitudinal direction L with the axis A of an adjacent trailing bone-anchor fixation hole 126. For example, the axis A of the at least one trailing bone-anchor fixation hole 126 can be in-plane with the axis A of the adjacent trailing bone-anchor fixation hole 126. Thus, the openings 124a and 124b of the trailing bone-anchor fixation hole 126 can be aligned along the longitudinal direction L with the openings 124a or 124b of an adjacent trailing bone-anchor fixation hole 126. In an aspect, the central bone-anchor axis A of each trailing bone-anchor fixation hole 126 can be parallel to the central bone-anchor axis A of an adjacent one of the trailing bone-anchor fixation holes 126. Alternatively, the central bone-anchor axis A of each trailing bone-anchor fixation hole 126 can be angularly offset from the central bone-anchor axis A of an adjacent one of the trailing bone-anchor fixation holes 126 such that the central bone-anchor axes A converge on one side of the intramedullary nail 101 and diverge on the other side.

Alternatively, the axis A of at least one trailing bone-anchor fixation hole 126 can be angularly offset along the longitudinal direction L from the axis A of an adjacent trailing bone-anchor fixation hole 126. For example, the axis A of the at least one trailing bone-anchor fixation hole 126 can be out of plane with the axis A of the adjacent trailing bone-anchor fixation hole 126. Thus, the openings 124a and 124b of each trailing bone-anchor fixation hole 126 can be out of alignment along the longitudinal direction L with the openings 124a and 124b of an adjacent trailing bone-anchor fixation hole 126. In other words, the openings 124a and 124b of each trailing bone-anchor fixation hole 126 at the outer surface 114 can be circumferentially offset from the openings 124a and 124b of an adjacent trailing bone-anchor fixation hole 126 at the outer surface 114. Thus, the central bone-anchor axis A of each trailing bone-anchor fixation hole 126 can be at a non-zero angle relative to the central bone-anchor axis A of an adjacent one of the trailing bone-anchor fixation holes 126.

The plurality of bone-anchor fixation holes 124 also includes at least one leading bone-anchor fixation hole 128. All of the at least one leading bone-anchor fixation holes 128 are offset from all of the at least one trailing bone-anchor fixation holes 126 along the longitudinal direction L. Each of the at least one leading bone-anchor fixation hole 128 extends entirely through the leading body portion 106 of the intramedullary nail 101. In an aspect, each of the at least one leading bone-anchor fixation hole 128 extends into the intramedullary nail 101 at a distance from the leading end 102 that is less than one half of the overall length $L_O$ of the intramedullary nail 101, such as a distance that is less than or equal to one third of the overall length $L_O$ of the intramedullary nail 101, such as a distance that is less than or equal to one quarter of the overall length $L_O$ of the intramedullary nail 101. Although a plurality of leading bone-anchor fixation holes 128 are shown, it will be understood that the intramedullary nail 101 can define as few as one leading bone-anchor fixation hole 128. In aspects having a plurality of leading bone-anchor fixation holes 128, the plurality of leading bone-anchor fixation holes 128 can be offset from one another along the longitudinal direction L.

Each leading bone-anchor fixation hole 128 can have an axis A that is aligned along the longitudinal direction L with the axis A of an adjacent leading bone-anchor fixation hole 128. For example, the leading bone-anchor fixation hole 128 and the adjacent leading bone-anchor fixation hole 128 can be in-plane with one another. Thus, the openings 124a and 124b of the leading bone-anchor fixation hole 128 can be aligned along the longitudinal direction L with the openings 124a and 124b of the adjacent distal bone-anchor fixation hole 128. Further, the central bone-anchor axis A of each leading bone-anchor fixation hole 128 can be parallel to the central bone-anchor axis A of an adjacent one of the leading bone-anchor fixation holes 128 or can be angularly offset from the central bone-anchor axis A of an adjacent one of the leading bone-anchor fixation holes 128 such that the central bone-anchor axes A converge on one side of the intramedullary nail 101 and diverge on the other side.

Alternatively, the axis A of at least one leading bone-anchor fixation hole 128 can be angularly offset from the axis A of an adjacent leading bone-anchor fixation hole 128 along the longitudinal direction L. For example, a leading bone-anchor fixation hole 128 and an adjacent leading bone-anchor fixation hole 128 can be out of plane with one another. As such, the openings 124a and 124b of each leading bone-anchor fixation hole 128 can be out of alignment along the longitudinal direction L with the openings 124a and 124b of an adjacent leading bone-anchor fixation hole 128. In other words, the openings 124a and 124b of each leading bone-anchor fixation hole 128 can be circumferentially offset from the openings 124a and 124b of an adjacent leading bone-anchor fixation hole 128. Thus, the central bone-anchor axis A of each leading bone-anchor fixation hole 128 can be at a non-zero angle relative to the central bone-anchor axis A of an adjacent one of the leading bone-anchor fixation holes 128.

Moreover, the axis A of at least one leading bone-anchor fixation hole 128 can be aligned with the axis A of a trailing bone-anchor fixation hole 126 along the longitudinal direction L. For example, the axis A of a leading bone-anchor fixation hole 128 can be in-plane with the axis A of a trailing bone-anchor fixation hole 126. As such, the openings 124a and 124b of the leading bone-anchor fixation hole 128 are aligned with the openings 124a and 124b of the trailing bone-anchor fixation hole 126 along the longitudinal direction L. Alternatively, the axis A of at least one leading bone-anchor fixation hole 128 can be angularly offset from the axis A of a trailing bone-anchor fixation hole 126. For example, the axis A of a leading bone-anchor fixation hole 128 can be out of plane with the axis A of a trailing bone-anchor fixation hole 126. As such, the openings 124a and 124b of the leading bone-anchor fixation hole 128 can be out of alignment with the openings 124a and 124b of the trailing bone-anchor fixation hole 126 along the longitudinal direction L. In other words, the openings 124a and 124b of the leading bone-anchor fixation hole 128 can be circumferentially offset from the openings 124a and 124b of a trailing bone-anchor fixation hole 126. Thus, the central bone-anchor axis A of the leading bone-anchor fixation hole 128 can be at a non-zero angle relative to the central bone-anchor axis A of the trailing bone-anchor fixation hole 126.

FIGS. 6 and 7 illustrate elevation views of a third side and a fourth side of the intramedullary nail 101, accordingly to aspects of this disclosure. The intramedullary nail 101 defines a compression slot 130 that extends into and through the intramedullary nail 101 in a direction substantially perpendicular to the central axis C. The compression slot 130 can intersect the cannulation 120. For instance, the compression slot 130 can extend into the outer surface 114 on a first side of the intramedullary nail 101 and out of the outer surface 114 on a second side of the intramedullary nail 101, opposite the first side. The compression slot 130 is a self-retaining compression slot that is configured to at least temporarily retain a compression member within. The compression slot 130 is configured to provide positional flexibility when the intramedullary nail assembly 100 is inserted into the medullary canal of the fractured long bone 20.

The compression slot 130 can be elongate along the leading direction L. In the illustrated aspect, the compression slot 130 extends into the trailing portion 108 of the intramedullary nail 101. It will be appreciated that the compression slot 130 can alternatively extend into the leading portion 106 of the intramedullary nail 101, or into both the leading and trailing portions 106 and 108 of the intramedullary nail 101. The portion of the intramedullary nail 101 that defines the compression slot 130 can define a cross-sectional distance, such as a diameter, that is greater than that of the other portions. Otherwise stated, the portion of the intramedullary nail 101 that defines the compression slot 130, such as the trailing portion 108, can define a cross-sectional area, such as a diameter, that is greater than that of one or both of the leading portion 106 and the intermediate portion 110.

The compression slot 130 can be positioned adjacent to trailing bone-anchor fixation holes 126. One or more of the trailing bone-anchor fixation holes 126 can be disposed longitudinally outward along the trailing direction T with respect to the compression slot 130, such that the compression slot 130 is disposed longitudinally between the trailing bone-anchor fixation holes 126 and the leading end 102. Alternatively, or additionally, one or more up to all of the trailing bone-anchor fixation holes 126 can be disposed longitudinally inward with respect to the compression slot 130, such that the trailing bone-anchor fixation holes 126 are disposed longitudinally between the compression slot 130 and the leading end 102. Similarly, if the compression slot 130 is disposed in the leading portion 106 of the intramedullary nail 101, the leading bone-anchor fixation holes 128 longitudinally outward along the leading direction L with respect to the compression slot 130, or the leading bone-anchor fixation holes 128 can alternatively or additionally be disposed longitudinally inward of the compression slot 130.

The intramedullary nail 101 may define a leading receiving slot or leading receiving element 121 (see FIG. 5). The receiving slot 121 extends from a respective one of the leading bone-anchor fixation holes 128. For example, an edge 123 of the tubular wall 122 of the intramedullary nail 101 that defines the one of the leading bone-anchor fixation holes 128 may extend about the tubular wall 122 to further define the leading receiving slot 121. The leading receiving slot 121 extends into and through the intramedullary nail 101 in a direction substantially perpendicular to the central axis C. In an aspect, the leading receiving slot 121 extends from the leading bone-anchor fixation hole 128 in the leading direction L. The leading receiving slot 121 can have a width that is different from, such as less than, a width of the respective one of the leading bone-anchor fixation holes 128. It will be appreciated that the leading receiving slot 121 may alternatively be defined by an edge of a compression slot in a substantially similar manner as the leading receiving slot 121 is defined by the leading bone-anchor fixation hole 128. Thus, it can be said that the leading receiving slot 121 extends from a hole that extends into the outer surface of the intramedullary nail 101, where the hole can be, for example, a bone-anchor fixation hole or a compression slot.

The intramedullary nail 101 may define a trailing receiving slot or trailing receiving element 131 (see FIG. 6). The receiving slot 131 extends from the compression slot 130. The receiving slot 131 can have a width that is different from, such as less than, a width of the compression slot 130. For example, an edge 132 of the tubular wall 122 of the intramedullary nail 101 that defines the inlay compression slot 130 may extend about the tubular wall 122 to further define the trailing receiving slot 131. The trailing receiving slot 131 extends into and through the intramedullary nail 101 in a direction substantially perpendicular to the central axis C. In an aspect, the trailing receiving slot 131 extends from the compression slot 130 in the trailing direction T. It will be appreciated that the trailing receiving slot 131 may alternatively be defined by an edge of at least one of the bone-anchor fixation holes 124 in a substantially similar manner as the trailing receiving slot 131 is defined by the compression slot 130. Thus, it can be said that the trailing receiving slot 131 extends from a hole that extends into the outer surface of the intramedullary nail 101, and that the hole can be, for example, a bone-anchor fixation hole or a compression slot.

FIG. 8 illustrates an elevation view of a fifth side of the intramedullary nail 101, according to an aspect of this disclosure. The inner surface 118 of the intramedullary nail 101 can define a recess 140 that extends from the second end 104 in the leading direction L. The recess 140 is configured to receive an alignment member 262 of the first inlay 200 within, as further explained below.

FIGS. 9-11 illustrate a perspective view of the first inlay 200, an elevation view of a first side of the first inlay 200, and a perspective view of a cross section of the first inlay 200 taken along line 10-10 in FIG. 10, according to aspects of this disclosure. The first inlay 200 is configured to be inserted into the cannulation 120 of the intramedullary nail 101, as explained in further detail below. The first inlay 200 includes a first inlay body 201 that is elongate from a first end 202 to a second end 204. The first end 202 can be considered to be a distal end or leading end, and can define a first terminal or outermost end of the first inlay body 201. The second end 204 can be considered to be a proximal end or trailing end and can define a second terminal or outermost end of the first inlay body 201. The first inlay 200 may comprise a polymeric material.

The first inlay body 201 is substantially elongate along a central pathway C' that extends from the trailing end 204 to the leading end 202 in a leading direction L'. In at least some aspect, the central pathway can be defined by a central axis C' of the first inlay body 201 that extends from the trailing end 204 to the leading end 202. The leading direction L' may be substantially parallel to the central axis C'. It will be appreciated that the central pathway or central axis C' of the first inlay body 201 can be straight or curved. Thus, the first inlay body 201 can be straight or curved as it extends along the central pathway or central axis C' from the trailing end 204 to the leading end 202. The first inlay body 201 can be inserted into the cannulation 120 of the intramedullary nail 101 such that the central axis C' of the first inlay body 201 substantially aligns with and/or is coaxial with the central axis C of the intramedullary nail 101.

The first inlay body 201 has a leading body portion 206 and a trailing body portion 208 adjacent to the leading portion 206 along the central axis C'. An interface between the leading body portion 206 and the trailing body portion 208 defines an inlay shoulder 209. The shoulder 209 may be defined by a difference between a cross-sectional dimension (e.g. diameter) of the trailing body portion 208 being greater than a cross-sectional dimension (e.g. diameter) of the leading body portion 206. The shoulder 209 defines a leading end of the trailing body portion 208 that includes a shoulder surface 211. The shoulder surface 211 may be angularly offset from, such as substantially perpendicular to, the central axis C'. In alternative aspects, the shoulder surface 211 may have a conical shape, curved shape, or other shape. It will be appreciated that the shoulder surface 211 corresponds to the shoulder surface 111 of the intramedullary nail 101 such that the shoulder surface 211 of the first inlay body 201 is configured to lie substantially flush against the shoulder surface 111 of the intramedullary nail 101 when the first inlay body 201 is positioned within the cannulation 120 of the intramedullary nail 101.

The first inlay body 201 has an outer surface 214 that extends from the leading body portion 206 to the trailing body portion 208. In an aspect, the shoulder surface 211 composes a portion of the outer surface 214. The outer surface 214 can extend from the trailing end 204 to the leading end 202. The outer surface 214 can define an outer-most perimeter of the first inlay body 201. Further, the outer surface 214 can have any suitable cross-sectional shape as desired. For example, the outer surface 214 can be substantially circular in cross section along a plane that is substantially perpendicular to the central axis C'. It will be appreciated that the outer surface 214 may be configured to correspond to the inner surface 118 of the intramedullary nail 101 such that, as the first inlay body 201 is inserted into the cannulation 120 of the intramedullary nail 101, the first inlay body 201 is axially moveable along the central axis C of the intramedullary nail 101.

With reference to FIG. 11, the first inlay body 201 has an inner surface 218 opposite the outer surface 214. The first inlay body 201 includes a tubular wall 222 between the inner surface 218 and the outer surface 214. The inner surface 218 defines a cannulation 220 that extends through the first inlay body 201 from the trailing end 204 to the leading end 202. The cannulation 220 can extend along the central axis C' of the first inlay body 201. The inner surface 218 can have a plurality of cross-sections along the central axis C', each cross-section defined in a plane that is perpendicular to the central axis C'. The inner surface 218 in each cross-section can have any suitable cross-sectional shape as desired. For example, the inner surface 218 in each cross-section can define a cross-sectional shape that is closed such as a circle, oval, square, rectangle, or other shape.

FIG. 12 illustrates an elevation view of a second side of the first inlay 200, opposite the first side, according to an aspect of this disclosure. The first inlay body 201 defines a plurality of bone-anchor fixation holes 224. Each bone-anchor fixation hole 224 is configured to receive a bone anchor so as to attach the intramedullary nail 101 to a bone when the first inlay 200 is positioned within the intramedullary nail 101. The bone-anchor fixation holes 224 can include one of more holes that can intersect the cannulation 220 of the first inlay body 201. In particular, each bone-anchor fixation hole 224 can extend into the outer surface 214 and at least partially, such as entirely, through the first inlay body 201. For instance, each bone-anchor fixation hole 224 can extend into the outer surface 214 on a first side of the first inlay body 201 and out of the outer surface 214 on a second side of the first inlay body 201, opposite the first side. Thus, each bone-anchor fixation hole 224 can extend from an opening 224a on a first side of the first inlay body 201 to an opening 224b on the second side of the first inlay body 201. As such, each bone-anchor fixation hole 224 can be considered to be a through hole, although aspects of the disclosure are not limited to through holes. At least some of the bone-anchor fixation holes 224 can extend through the tubular wall 222 on a first side of the first inlay body 201 and through the tubular wall 222 on a second side of the first inlay body 201, opposite the first side.

In an aspect, each bone-anchor fixation hole 224 of the first inlay body 201 is configured to align with a corresponding bone-anchor fixation hole 126 defined by the trailing portion 108 of the intramedullary nail 101 when the first inlay body 201 is positioned within the cannulation 120. As such, a through hole is formed through the intramedullary nail assembly 100 that extends through the bone-anchor fixation hole 224 of the first inlay body 201 and the corresponding bone-anchor fixation hole 126 of the intramedullary nail 101. In an aspect, the bone-anchor fixation holes 224 may have a shape that is substantially congruent to a shape of the corresponding bone fixation holes 126. In an aspect, the cross-sectional dimension (e.g. diameter) of the bone-anchor fixation holes 224 is smaller than the cross-sectional dimension (e.g. diameter) of the corresponding bone-anchor fixation holes 126 of the intramedullary nail 101. The cross-sectional dimension of the bone-anchor fixation holes 224 allows a bone anchor screw that is inserted in the intramedullary nail assembly 100 through the bone-anchor fixation hole 224 of the first inlay body 201 and through a respective bone-anchor fixation hole 124 of the intramedullary nail 101 to contact the first inlay body 201 to further secure the screw to the intramedullary nail assembly 100.

FIGS. 13 and 14 illustrate a front view and a back view of the first inlay 200, respectively, according to aspects of this disclosure. The first inlay body 201 defines an inlay compression slot 230 that extends into and through the first inlay body 201 in a direction substantially perpendicular to the central axis C'. The inlay compression slot 230 can intersect the cannulation 220. For instance, inlay the compression slot 230 can extend into the outer surface 214 on a first side of the first inlay body 201 and out of the outer surface 214 on a second side of the first inlay body 201, opposite the first side. The inlay compression slot 230 is a self-retaining compression slot that is configured to at least temporarily retain a compression member within.

The inlay compression slot 230 of the first inlay body 201 is configured to align with the compression slot 130 defined by the trailing portion 108 of the intramedullary nail 101 when the first inlay body 201 is positioned with the cannulation 120. As such, a slot is formed through the intramedullary nail assembly 100 that extends through the inlay compression slot 230 of the first inlay body 201 and the corresponding compression slot 130 of the intramedullary nail 101. The inlay compression slot 230 may be relieved congruent to the compression slot 130. In an aspect, inlay compression slot 230 may have a shape that is substantially congruent to a shape of the corresponding compression slot 130. The inlay compression slot 230 may have a cross-sectional dimension (e.g. diameter and/or width) that is substantially the same as a cross-sectional dimension (e.g. diameter and/or width) of the corresponding compression slot 130 of the intramedullary nail 101. In an alternative aspect, the cross-sectional dimension (e.g. diameter and/or width) of the inlay compression slot 230 may be smaller than the cross-sectional dimension (e.g. diameter and/or width) of the corresponding compression slot 130 of the intramedullary nail 101. The alignment of the inlay compression slot 230 with the compression slot 130 is to provide positional flexibility when the intramedullary nail assembly 100 is inserted into the medullary canal of the fractured long bone 20.

The first inlay 200 includes at least one engagement feature that is configured to engage the intramedullary nail 101 so as to limit one or both of (1) translation of the first inlay 200 relative to the intramedullary nail 101 along the central axis C' and (2) rotation of the first inlay 200 relative to the intramedullary nail 101 about the central axis C'. The at least one engagement feature can include one or more, up to all, of an engagement member 250, a projection 260, and an alignment member 262. Each engagement feature can extend from the outer surface 214 of the first inlay 200, such as outwardly from the outer surface 214. It will be understood, however, that each engagement feature could alternatively extend inwardly from the outer surface 214.

The first inlay 200 can include the engagement member 250. In an aspect, the engagement member 250 is located adjacent to the inlay compression slot 230. In an alternative aspect, the engagement member 250 may be located adjacent to at least one of the bone-anchor fixation holes 224, or another location on the outer surface 214 of the first inlay body 201. The engagement member 250 can have a shape that conforms to a shape of the receiving slot 131 of the intramedullary nail 101. The engagement member 250 is configured to be received within the receiving slot 131 so as to limit one or both of the translation of the first inlay 200 relative to the intramedullary nail 101 along the trailing direction T and rotation of the first inlay 200 about the central axis C'. The engagement member 250 extends radially outward from the outer surface 214. The engagement member 250 may be resiliently attached to the first inlay body 201 such that when the first inlay body 201 is inserted into the cannulation 120 of the intramedullary nail 101 the engagement member 250 flexes radially inwardly toward the central axis C', and when the engagement member 250 is aligned with the receiving slot 131, the engagement member 250 flexes radially outward so as to be received in the receiving slot 131. Thus, the engagement member 250 can be biased radially outward.

The first inlay body 201 may define an engagement slot 252. The engagement slot 252 may extend from at least one of the bone-anchor fixation holes 224 or the inlay compression slot 230. For example, an edge 232 of the tubular wall 222 of the first inlay body 201 that defines an opening to the inlay compression slot 230 may extend about the tubular wall 222 to further define the engagement slot 252. The engagement slot 252 extends into and through the first inlay body 201 in a direction substantially perpendicular to the central axis C'. The engagement member 250 may extend into the engagement slot 252 from the edge 232. In an aspect, the engagement member 250 extends from the edge 232 into the engagement slot 252 in the leading direction L'. The engagement member 250 can be attached to the body 201 so as to form a hinge that permits the engagement member 250 to flex radially inward and outward.

The first inlay body 201 may further include at least one radial projection 260. The radial projection 260 is configured to contact the inner surface 118 of the intramedullary nail 101 so as to further limit one or both of translation of the of the first inlay 200 along the trailing and leading directions T and L and/or rotation of the first inlay 200 about the central axis C. The radial projection 260 extends radially out from the outer surface 214 on the leading body portion 206. The radial projection 260 has a cross sectional dimension (e.g. diameter) that is greater than a cross sectional dimension (e.g. diameter) of the outer surface 214 of the leading body portion 206. In an aspect, the radial projection 260 can be located about the outer surface 214 that defines the bone anchor hole 224 closest to the leading end 202 of the first inlay body 201. For example, the radial projection 260 can be aligned with the bone anchor hole 224 about a circumference of the outer surface 214. In some examples, the at least one radial projection 260 can include a pair of radial projections that extend radially out from the outer surface 214 in opposite directions.

The first inlay body 201 may further include the alignment member 262. The alignment element 262 is configured to be received within a recess defined by the inner surface 118 of the intramedullary nail 101 to rotationally align the first inlay body 201 with the intramedullary nail 101. The alignment member 262 extends radially outward from the outer surface 214 of the trailing body portion 208. The alignment member 262 has a cross sectional dimension (e.g. diameter) that is greater than a cross sectional dimension (e.g. diameter) of the outer surface 214 of the trailing body portion 208.

Figure 15:
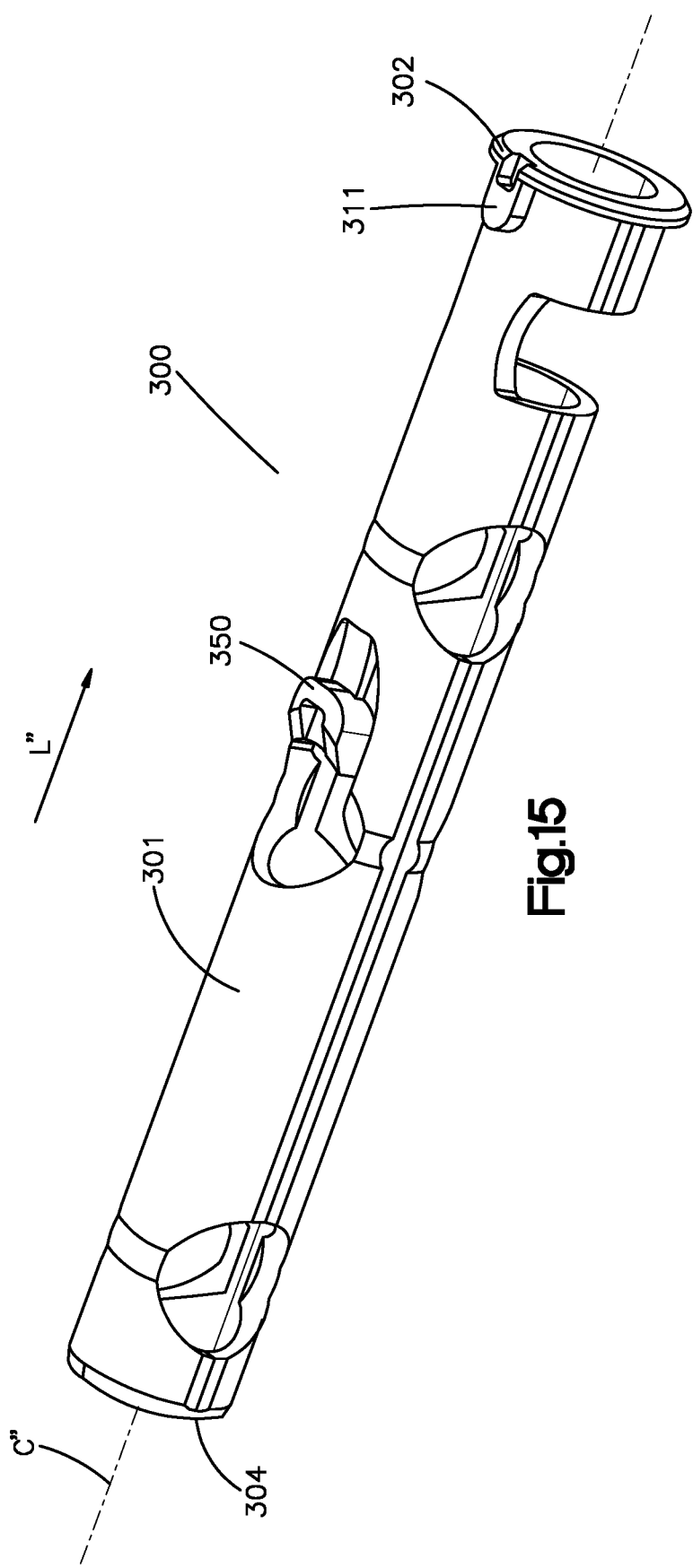
FIG. 15 illustrates a perspective view of a second inlay, according to an aspect of this disclosure.

FIGS. 15-17 illustrate a perspective view of the second inlay 300, an elevation view of the second inlay 300, and a perspective view of a cross section of the second inlay 300 taken along line 16-16 in FIG. 16, according to aspects of this disclosure. The first inlay 300 includes a second inlay body 301 that is elongate from a first end 302 to a second end 304. The first end 302 can be considered to be a distal end or leading end, and can define a first terminal or outermost end of the second inlay body 301. The second end 304 can be considered to be a proximal end or trailing end and can define a second terminal or outermost end of the second inlay body 301. The second inlay 300 may comprise a polymeric material.

The second inlay body 301 is substantially elongate along a central pathway that extends from the trailing end 304 to the leading end 302 in a leading direction L". The central pathway can be defined by a central axis C" of the second inlay body 301 that extends from the trailing end 304 to the leading end 302. The leading direction L" may be substantially parallel to the central axis C". It will be appreciated that the central pathway or central axis C" of the second inlay body 301 can be straight or curved. The second inlay body 301 can be inserted into the cannulation 120 of the intramedullary nail 101 such that the central axis C" of the second inlay body 301 substantially aligns with and/or is coaxial with the central axis C of the intramedullary nail 101.

The leading end 302 of the second inlay body 301 may define a projection 309. The projection 309 extends radially outward from an outer surface 314 of the second inlay body 301, such that a cross sectional dimension (e.g. diameter) of the projection 309 is greater than a cross sectional dimension (e.g. diameter) of the outer surface 314. The projection 309 is configured to substantially prevent further axial movement of the second inlay body 301 into the cannulation 120 of the intramedullary nail 101. The leading end 302 may also define an alignment member 311. The alignment member 311 extends radially outward from the outer surface 314. In an aspect, the alignment member 311 is positioned adjacent to the projection 309 along the leading direction L". The alignment member 311 is configured to rotationally align the second inlay body 301 with the intramedullary nail 101.

The outer surface 314 of the second inlay body 301 extends from the leading end 302 to the trailing end 304. The outer surface 314 can define an outer-most perimeter of the second inlay body 301. Further, the outer surface 314 can have any suitable cross-sectional shape as desired. For example, the outer surface 314 can be substantially circular in cross section along a plane that is substantially perpendicular to the central axis C". It will be appreciated that the outer surface 314 may be configured to correspond to the inner surface 118 of the intramedullary nail 101 such that, as the second inlay body 301 is inserted into the cannulation 120 of the intramedullary nail 101, the second inlay body 301 is axially moveable along the central axis C of the intramedullary nail 101.

With reference to FIG. 17, the second inlay body 301 has an inner surface 318 opposite the outer surface 314. The second inlay body 301 includes a tubular wall 322 between the inner surface 318 and the outer surface 314. The inner surface 318 defines a cannulation 320 that extends through the second inlay body 301 from the trailing end 304 to the leading end 302. The cannulation 320 can extend along the central axis C" of the second inlay body 301. The inner surface 318 can have a plurality of cross-sections along the central axis C", each cross-section defined in a plane that is perpendicular to the central axis C". The inner surface 318 in each cross-section can have any suitable cross-sectional shape as desired. For example, the inner surface 318 in each cross-section can define a cross-sectional shape that is closed such as a circle, oval, square, rectangle, or other shape.

Figure 18:
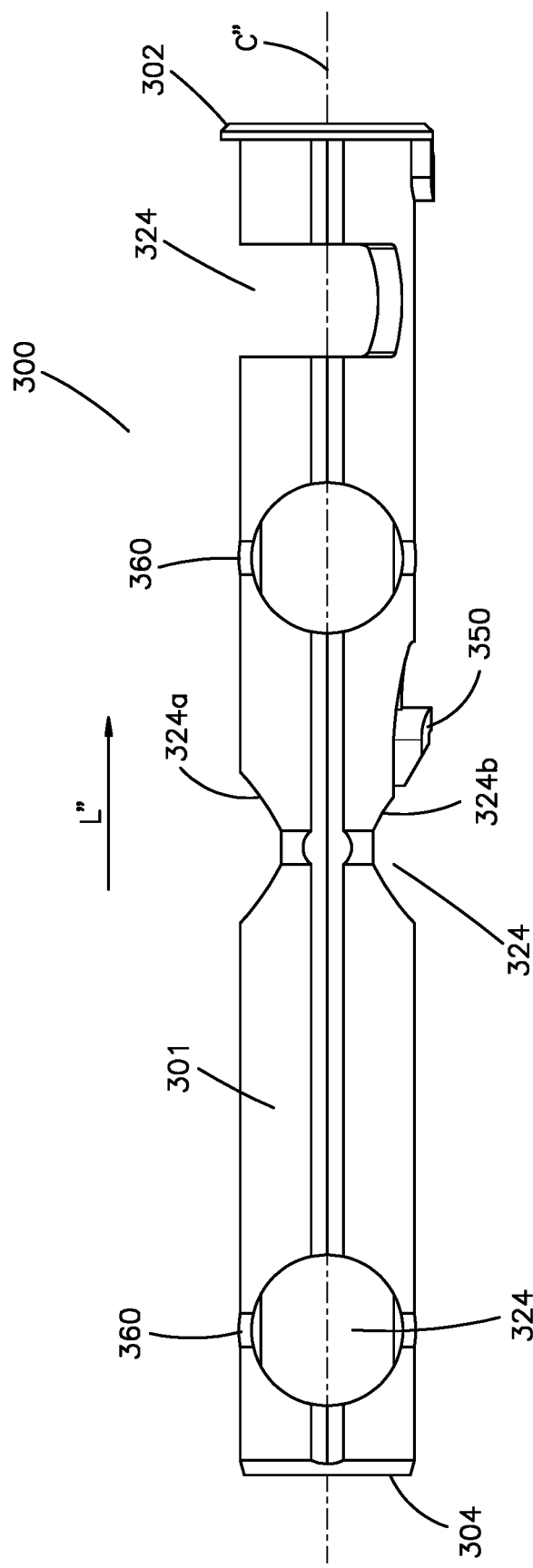
FIG. 18 illustrates an elevation view of a second side of the second inlay shown in FIG. 16, opposite the first side.

FIG. 18 illustrates a bottom view of the second inlay 300, according to an aspect of this disclosure. The second inlay body 301 defines a plurality of bone-anchor fixation holes 324. Each bone-anchor fixation hole 324 is configured to receive a bone anchor so as to attach the intramedullary nail 101 to a bone when the second inlay 300 is positioned within the intramedullary nail 101. The bone-anchor fixation holes 324 can include one of more holes that can intersect the cannulation 320 of the second inlay body 301. In particular, each bone-anchor fixation hole 324 can extend into the outer surface 314 and at least partially, such as entirely, through the second inlay body 301. For instance, each bone-anchor fixation hole 324 can extend into the outer surface 314 on a first side of the second inlay body 301 and out of the outer surface 314 on a second side of the second inlay body 301, opposite the first side. Thus, each bone-anchor fixation hole 324 can extend from an opening 324a on a first side of the second inlay body 301 to an opening 324b on the second side of the second inlay body 301. As such, each bone-anchor fixation hole 324 can be considered to be a through hole, although aspects of the disclosure are not limited to through holes. At least some of the bone-anchor fixation holes 324 can extend through the tubular wall 322 on a first side of the second inlay body 301 and through the tubular wall 322 on a second side of the second inlay body 301, opposite the first side.

In an aspect, each bone-anchor fixation hole 324 of the second inlay body 301 is configured to align with a corresponding bone-anchor fixation hole 128 defined by the leading portion 106 of the intramedullary nail 101 when the second inlay body 301 is positioned within the cannulation 120. As such, a through hole is formed through the intramedullary nail assembly 100 that extends through the bone-anchor fixation hole 324 of the second inlay body 301 and the corresponding bone-anchor fixation hole 128 of the intramedullary nail 101. In an aspect, the bone-anchor fixation holes 324 may have a shape that is substantially congruent to a shape of the corresponding bone fixation holes 128. The shape of the openings 324a and the bone-anchor fixation holes 324 allows for dynamization during the bone healing process. In an aspect, the cross-sectional dimension (e.g. diameter) of the bone-anchor fixation holes 324 may be smaller than the cross-sectional dimension (e.g. diameter) of the corresponding bone-anchor fixation holes 128 of the intramedullary nail 101.

FIGS. 19 and 20 illustrate elevation views of a third and a fourth side of the second inlay 300, respectively, according to aspects of this disclosure. In an alternative example (not shown), the second inlay body 301 may define an inlay compression slot (not illustrated) that extends into and through the second inlay body 301 in a direction substantially perpendicular to the central axis C". The inlay compression slot can intersect the cannulation 320. For instance, inlay the compression slot can extend into the outer surface 314 on a first side of the second inlay body 301 and out of the outer surface 314 on a second side of the second inlay body 301, opposite the first side. The inlay compression slot is a self-retaining compression slot that is configured to at least temporarily retain a compression member within.

The inlay compression slot of the second inlay body 301 is configured to align with a compression slot (not shown) defined by the leading portion 106 of the intramedullary nail 101 when the second inlay body 301 is positioned with the cannulation 120. As such, a slot is formed through the intramedullary nail assembly 100 that extends through the inlay compression slot of the second inlay body 301 and the corresponding compression slot of the intramedullary nail 101. The inlay compression slot may be relieved congruent to the compression slot of the intramedullary nail 101. In an aspect, the inlay compression slot of the second inlay body 301 may have a shape that is substantially congruent to a shape of the corresponding compression slot of the intramedullary nail 101. The inlay compression slot of the second inlay body 301 may have a cross-sectional dimension (e.g. diameter and/or width) that is substantially the same as a cross sectional dimension (e.g. diameter and/or width) of the corresponding compression slot of the intramedullary nail 101. In an alternative aspect, the cross-sectional dimension (e.g. diameter and/or width) of the inlay compression slot of the second inlay body 301 may be smaller than the cross-sectional dimension (e.g. diameter and/or width) of the corresponding compression slot of the intramedullary nail 101. The alignment of the inlay compression slot of the second inlay body 301 with the compression slot of the intramedullary nail 101 is to provide positional flexibility when the intramedullary nail assembly 100 is inserted into the medullary canal of the fractured long bone 20.

The second inlay 300 includes at least one engagement feature that is configured to engage the intramedullary nail 101 so as to limit one or both of (1) translation of the second inlay 300 relative to the intramedullary nail 101 along the central axis C' and (2) rotation of the second inlay 300 relative to the intramedullary nail 101 about the central axis C'. The at least one engagement feature can include one or more, up to all, of a projection 309, an engagement member 350, a projection 360, and an alignment member 311. Each engagement feature can extend from the outer surface 314 of the first inlay 300, such as outwardly from the outer surface 314. It will be understood, however, that each engagement feature could alternatively extend inwardly from the outer surface 314.

The second inlay body 301 can include the engagement member 350. In an aspect, the engagement member 350 is located adjacent to one of the bone-anchor fixation holes 324. In an alternative aspect, the engagement member 350 may be located adjacent to a compression slot, or another location on the outer surface 314 of the second inlay body 301. The engagement member 350 is configured to be received within an engagement or receiving slot 352 so as to limit one or both of the translation of the second inlay 300 relative to the intramedullary nail 101 along the leading direction L and rotation of the second inlay 200 about the central axis C. The engagement member 350 extends radially outward from the outer surface 314. The engagement member 350 may be flexible such that when the second inlay body 301 is inserted into the cannulation 120 of the intramedullary nail 101 the engagement member 350 flexes radially inwardly toward the central axis C".

The second inlay body 301 may define a receiving slot 352. The receiving slot 352 may extend from at least one of the bone-anchor fixation holes 324 or an inlay compression slot. For example, an edge 332 of the tubular wall 322 of the second inlay body 301 that defines an opening to one of the bone bone-anchor fixation holes 324 may extend about the tubular wall 322 to further define the receiving slot 352. The receiving slot 352 extends into and through the second inlay body 301 in a direction substantially perpendicular to the central axis C". The engagement member 350 may extend into the receiving slot 352 from the edge 332. In an aspect, the engagement member 350 extends into the receiving slot 352 from the edge 332 in a trailing direction T". The trailing direction T" is opposite the leading direction L".

The second inlay body 301 may further include one or more radial projections 360 (see FIG. 18). The radial projection 360 extends radially about the outer surface 314 of the second inlay body 301. In an aspect, each radial projection 360 can extend about the outer surface 314 at a location where the bone-anchor fixation holes 324 are positioned. For example, each radial projection 360 can be aligned with the bone anchor hole 424 about a circumference of the outer surface 214. The radial projection 360 has a cross sectional dimension (e.g. diameter) that is greater than a cross sectional dimension (e.g. diameter) of the outer surface 314. The radial projection 360 is configured to provide stability between the second inlay 300 and the intramedullary nail 101.

FIG. 21 illustrates a perspective view of an inlay 400, according to an aspect of this disclosure. The inlay 400 is configured to be inserted through the cannulation 120 of the intramedullary nail 101. The inlay 400 may also be referred to as an "eyelet." The inlay 400 has a body 401 that extends from a first end 402 to a second end 404 along a eyelet direction E. The eyelet body 401 extends along a central axis C''' that extends from the first end 402 to the second end 404 in the eyelet direction E. The eyelet body 401 can be inserted into one of the bone-anchor fixation holes 124 of the intramedullary nail 101 such that the central axis C''' of the eyelet body 401 substantially aligns with and/or is coaxial with the axis A of the respective bone-anchor fixation hole 124.

The inlay body 401 has an inner surface 418 opposite an outer surface 414. The inlay body 401 includes a tubular wall 422 between the inner surface 418 and the outer surface 414. The inner surface 418 defines a cannulation 420 that extends through the eyelet body 401 in a direction that is angularly offset from, such as substantially perpendicular to, the eyelet direction E. The cannulation 420 is configured to align with the cannulation 120 of the intramedullary nail 101 when the inlay body 401 is received in the respective bone-anchor fixation hole 124.

The eyelet body 401 defines a bone-anchor fixation hole 424 that extends through the eyelet body 401 from the first end 402 to the second end 404 along the central axis C'''. The bone-anchor fixation hole 424 is configured to receive a bone anchor so as to attach the intramedullary nail 101 to a bone when the inlay 400 is positioned within the intramedullary nail 101. The bone-anchor fixation hole 424 intersects the cannulation 420 of the inlay body 401. In an aspect, a cross-sectional dimension of the hole 424 is less than a diameter of the hole 124 intramedullary nail 101 such that a bone anchor positioned within the hole 124 can bite into the inlay 400.

The inlay 400 includes at least one engagement feature that is configured to engage the intramedullary nail 101 so as to limit one or both of (1) translation of the inlay 400 relative to the intramedullary nail 101 along the central axis C' and (2) rotation of the inlay 400 relative to the intramedullary nail 101 about the central axis C'. The at least one engagement feature can include one or more, up to all, of an engagement member 450 and a projection 460. Each engagement feature can extend from the outer surface 414 of the inlay 400, such as outwardly from the outer surface 414. It will be understood, however, that each engagement feature could alternatively extend inwardly from the outer surface 414.

The inlay body 401 can include the at least one engagement member 450. The engagement member 450 is configured to engage the intramedullary nail 101 so as to limit translation along the axis A of the respective bone-anchor fixation hole 124 to which the inlay 400 is affixed. In an aspect, the engagement member 450 is located at the second end 404 of the eyelet body 401. In an alternative aspect, the engagement member 450 may be located at another location on the outer surface 414 of the eyelet body 401. The engagement member 450 extends radially outward from the outer surface 414. The engagement member 450 may be resilient such that when the eyelet body 401 is inserted into a bone-anchor fixation hole of the intramedullary nail 101 the engagement member 450 flexes radially inwardly toward the central axis C'''.

In an aspect, the at least one engagement member 450 can include a pair of engagement members 450a, 450b on opposed sides. As the inlay 400 is inserted into the intramedullary nail 101, the engagement members 450a, 450b flex inwardly toward the central axis C''' and flex outwardly after the elements 450a, 450b are inserted so as to engage the intramedullary nail 101. The engagement members 450a, 450b can be biased radially outwards so that it springs back automatically.

The inlay body 401 may further include at least one radial projection 460. The radial projection 460 is configured to engage the intramedullary nail 101 so as to limit translation along the axis A of the respective bone-anchor fixation hole 124 to which the inlay 400 is affixed. The radial projection 460 is configured to limit translation along the axis A in a direction opposite to the direction that the at least one engagement member 450 limits translation. The radial projection 460 is also configured to align the inlay 400 within the respective bone-anchor fixation hole 124 so that the cannulation 420 of the inlay body 401 aligns with the cannulation of the intramedullary nail 101. The radial projection 460 extends radially outward from the outer surface 414. In an aspect, the radial projection 460 is located at or toward the first end 402 of the eyelet body 401. The radial projection 460 has a cross sectional dimension (e.g. diameter) that is greater than a cross sectional dimension (e.g. diameter) of the outer surface 414 of the eyelet body 401.

FIG. 22 illustrates a perspective view of the inlay 400 positioned within a bone-anchor fixation hole 124 of the intramedullary nail 101 (note—the intramedullary nail 101 is shown as transparent to illustrate the position of inlay 400). The engagement member 450 may removably connect to an edge or chamfer defining the opening 124a,b of the bone-anchor fixation hole 124. In an aspect, the removable connection can be a snap-fit connection that creates an audible click when locked into place. When the inlay 400 is positioned within the intramedullary nail 101, a contact between the radial projection 460 of the eyelet 400 and the tubular wall 122 of the intramedullary nail 101 provides stability between the eyelet 400 and the intramedullary nail 101 such that circumferential movement of the eyelet 400 relative to the intramedullary nail 101 is reduced. In an aspect, the tubular wall 122 may define at least one recess that corresponds to the at least one radial projection 460 so that the radial projection 460 can be positioned within the recess.

Figure 23:
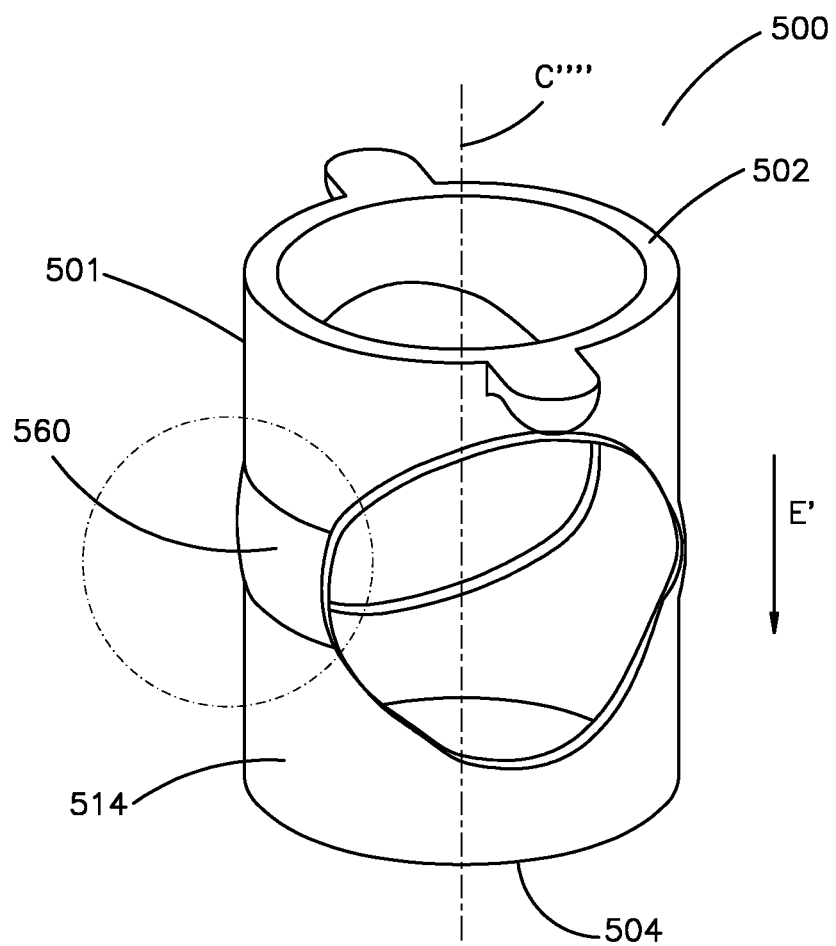
FIG. 23 illustrates a perspective view of an alternative inlay, according to an aspect of this disclosure.

FIG. 23 illustrates a perspective view of an alternative eyelet 500, according to an aspect of this disclosure. Portions of the aspects disclosed in FIG. 23 regarding eyelet 500 are similar to aspects described above in FIGS. 22 and 23 and those portions function similarly to those described above. The eyelet 500 has a body 501 that extends from a first end 502 to a second end 504 along a eyelet direction E'. The eyelet body 501 extends along a central axis C'''' that extends from the first end 502 to the second end 504 in the eyelet direction E'. The eyelet body 501 can be inserted into one of the bone-anchor fixation holes 124 of the intramedullary nail 101 such that the central axis C'''' of the eyelet body 501 substantially aligns with and/or is coaxial with the axis A of the respective bone-anchor fixation hole 124.

The eyelet body 501 may further include at least one radial projection 560. The radial projection 560 extends radially about an outer surface 514. In an aspect, the radial projection 560 is located between the first end 502 and the second end 504 of the eyelet body 501. In an aspect, the radial projection 560 is located about a cannulation 520 defined by the outer surface 514. For example, the radial projection 560 can be aligned with the bone anchor hole about a circumference of the outer surface 514. The radial projection 560 has a cross sectional dimension (e.g. diameter) that is greater than a cross sectional dimension (e.g. diameter) of the outer surface 514 of the eyelet body 501. The at least one radial projection 560 can include a pair of radial projections 560 that extend from the outer surface 514 is opposite directions.

Figure 26:
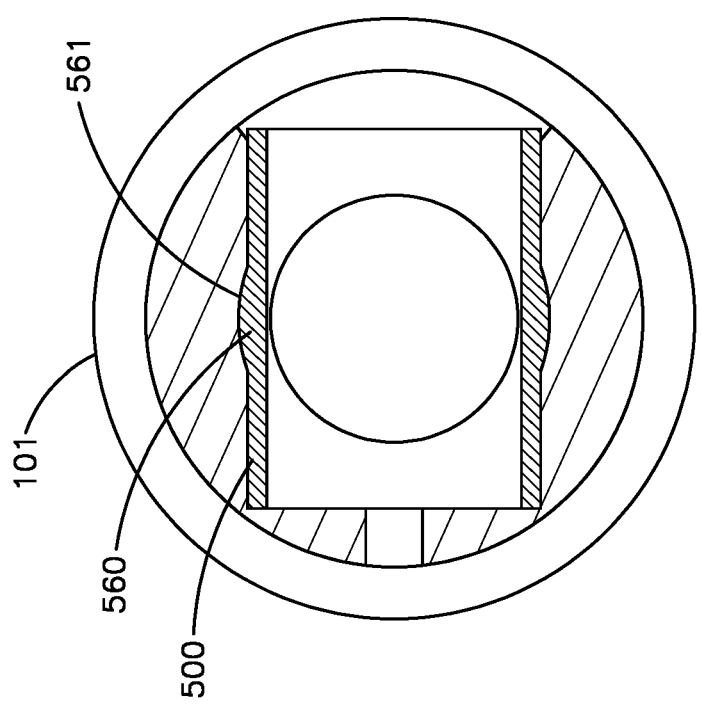
FIG. 26 illustrates a cross-sectional view of the inlay shown in FIG. 23 positioned within a bone-anchor fixation hole of an intramedullary nail taken along line 25-25 shown in FIG. 25.

FIGS. 24 and 25 illustrate a side view and a top view, respectively, of the eyelet 500 positioned within a bone-anchor fixation hole 124 of the intramedullary nail 101 (note—the intramedullary nail 101 is shown as transparent to illustrate the position of eyelet 500). FIG. 26 illustrates a cross-sectional view of the eyelet 500 positioned within a bone-anchor fixation hole 124 of the intramedullary nail 101 taken along line 25-25 shown in FIG. 25. The radial projection 560 may contact the inner surface 118 of the intramedullary nail 101 to removably secure the eyelet 500 within the bone-anchor fixation hole 124 of the intramedullary nail 101 In an aspect, the radial projection 560 may be received within a recess 561 defined by a surface (not labeled) of the bone-anchor fixation hole 124. When the eyelet 500 is positioned within the intramedullary nail 101, a contact between the radial projection 560 of the eyelet 500 and the surface of the bone-anchor fixation hole 124 provides stability between the eyelet 500 and the intramedullary nail 101 such that linear movement of the eyelet 500 along the axis A of the bone-anchor fixation hole 124 is reduced.

Figure 27:
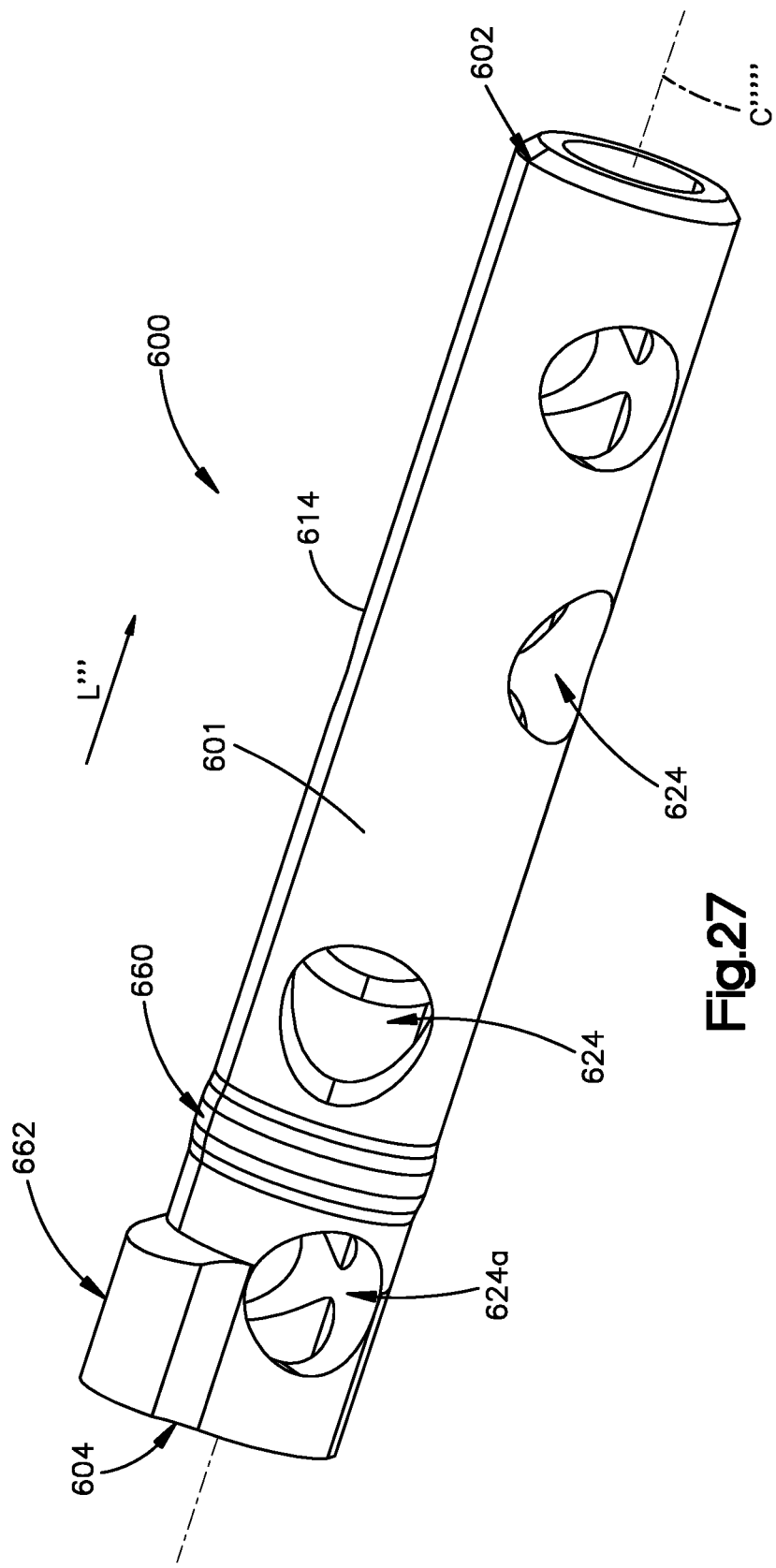
FIG. 27 illustrates a perspective view of an alternative inlay, according to an aspect of this disclosure.

FIG. 27 illustrates a perspective view of an alternative inlay 600, according to an aspect of this disclosure. Portions of the aspects disclosed in FIG. 27 regarding inlay 600 are similar to aspects described above in FIGS. 8 and 20 regarding the first inlay 200 and the second inlay 300 and those portions function similarly to those described above. The inlay 600 has a body 601 that extends from a trailing end 604 to a leading end 602 along a leading direction L'''. The inlay body 601 extends along a central axis C'''' that extends from the trailing end 604 to the leading end 602 in the leading direction L'''. The inlay 600 is configured to be inserted into the cannulation 120 of the intramedullary nail 101 such that the central axis C'''' of the inlay body 601 substantially aligns with and/or is coaxial with the central axis C of the intramedullary nail 101.

The inlay body 601 may further include at least one radial projection 660. The radial projection 660 is configured to contact the inner surface 118 of the intramedullary nail 101 so as to further limit one or both of translation of the of the inlay 600 along the trailing and leading directions T and L and/or rotation of the inlay 600 about the central axis C. The radial projection 660 extends radially out from an outer surface 614 on the body 601. The radial projection 660 has a cross sectional dimension (e.g. diameter) that is greater than a cross sectional dimension (e.g. diameter) of the outer surface 614 of the body 601. The radial projection 660 can be positioned closer to the trailing end 604 than to the leading end 602. For instance, the radial projection 660 can be positioned between a trailing most bone-anchor fixation hole 624a and bone-anchor fixation holes 624 positioned distally along the body 601 from the bone-anchor fixation hole 624a. In one example, the radial projection 660 can be positioned between the trailing most bone-anchor fixation hole 624a and an immediately adjacent bone-anchor fixation hole 624.

The inlay body 601 may further include an alignment member 662 (e.g. keying feature). The alignment element 662 is configured to be received within a recess defined by the inner surface 118 of the intramedullary nail 101 to rotationally align the inlay body 601 with the intramedullary nail 101. The alignment member 662 extends radially outward from the outer surface 614 of the body 601. The alignment member 662 has a cross sectional dimension (e.g. diameter) that is greater than a cross sectional dimension (e.g. diameter) of the outer surface 614 of the body 601.

Referring back to FIGS. 3, 9, and 15, the intramedullary nail assembly 100 can be assembled by inserting one or both of the first inlay 200 and the second inlay 300 into the intramedullary nail 101. The first inlay 200 is inserted into the cannulation 120 of the intramedullary nail 101 in the leading direction L through the second end 104 and into the trailing body portion 108. The first inlay 200 is moved into the cannulation 120 until the shoulder surface 211 of the first inlay body 201 abuts against the shoulder surface 111 of the intramedullary nail 101. The contact between the shoulder surfaces 111 and 211 substantially prevents axial movement of the first inlay 200 further through the cannulation 120 in the leading direction L. After the first inlay 200 is inserted into the cannulation 120, at least one of the bone-anchor fixation holes 224 and the compression slot 230 of the first inlay 200 align with at least one of the trailing bone-anchor fixation holes 126 and the compression slot 130 of the intramedullary nail 101, respectively.

In an aspect, after the first inlay 200 is positioned within the intramedullary nail 101, a contact between the radial projection 260 of the first inlay 200 and the inner surface 118 of the intramedullary nail 101 provides stability between the first inlay 200 and the intramedullary nail 101 such that radial movement of the leading body portion 206 of the first inlay 200 relative to the intramedullary nail 101 is limited or prevented altogether. The alignment member 262 of the first inlay 200 is configured to be received within the recess 140 (see FIG. 8) defined by the inner surface 118 of the intramedullary nail 101 so as to circumferentially align the first inlay 200 with the intramedullary nail 101.

During insertion of the first inlay 200 into the intramedullary nail 101, the engagement member 250 flexes radially inwardly. After the first inlay 200 is inserted, the engagement member 250 engages the receiving slot or element 131. In an aspect, the engagement member 250 moves radially outward into the receiving slot 131 of the intramedullary nail 101. The engagement between the engagement member 250 and the receiving slot 131 removably locks the first inlay 200 within the cannulation 120 of the intramedullary nail 101. In an aspect, the removable lock between the engagement member 250 and the intramedullary nail 101 substantially prevents linear and rotational movement between the first inlay 200 and the nail 101. In an aspect, the engagement member 250 and the receiving slot 131 form a snap-fit connection, such that the engagement member 250 snaps into the receiving slot 131 after the engagement member 250 aligns with the receiving slot 131. The engagement member 250 may be disengaged from the receiving slot 131 by applying a force to the engagement member 250 radially inward toward the central channel C of the nail 101 until the engagement member 250 is spaced apart from the receiving slot 131. In an aspect, the engagement between the engagement member 250 and the receiving slot 131 locks or fixedly locks the first inlay 200 within the cannulation 120 of the intramedullary nail 101, such that removal of the first inlay 200 from the cannulation 120 is substantially prevented.

The second inlay 300 is inserted into the cannulation 120 of the intramedullary nail 101 in the trailing direction T through the first end 102 and into the leading body portion 106. The second inlay 300 is moved into the cannulation 120 until the projection 309 against the first end 102 of the intramedullary nail 101. The contact between the projection 309 and the first end 102 of the intramedullary nail 101 substantially prevents axial movement of the second inlay 300 further through the cannulation 120 in the trailing direction T. After the second inlay 300 is inserted into the cannulation 120, at least one of the bone-anchor fixation holes 324 and the compression slot of the second inlay 300 align with at least one of the leading bone-anchor fixation holes 128 and the compression slot 130 of the intramedullary nail 101, respectively.

In an aspect, after the second inlay 300 is positioned within the intramedullary nail 101, a contact between the radial projection 360 of the second inlay 300 and the inner surface 118 of the intramedullary nail 101 provides stability between the second inlay 300 and the intramedullary nail 101 such that circumferential movement of the second inlay 300 relative to the intramedullary nail 101 is reduced. The alignment member 311 of the second inlay 300 is configured to be received within a recess defined by the inner surface 118 of the intramedullary nail 101 so as to circumferentially align the second inlay 300 with the intramedullary nail 101.

During insertion of the second inlay 300 into the intramedullary nail 101, the engagement member 350 flexes radially inwardly. After the second inlay 300 is inserted, the engagement member 350 engages the leading receiving slot or element 121. In an aspect, the engagement member 350 moves radially outward into the receiving slot 121 of the intramedullary nail 101. The engagement between the engagement member 350 and the receiving slot 121 removably locks the second inlay 300 within the cannulation 120 of the intramedullary nail 101. In an aspect, the removable lock between the engagement member 350 and the intramedullary nail 101 substantially prevents linear and rotational movement between the second inlay 300 and the nail 101. In an aspect, the engagement member 350 and the receiving slot 121 form a snap-fit connection, such that the engagement member 350 snaps into the receiving slot 121 after the engagement member 350 aligns with the receiving slot 121. The engagement member 350 may be disengaged from the receiving slot 121 by applying a force to the engagement member 350 radially inward toward the central channel C of the nail 101 until the engagement member 350 is spaced apart from the receiving slot 121. In an aspect, the engagement between the engagement member 350 and the receiving slot 121 locks or fixedly locks the second inlay 300 within the cannulation 120 of the intramedullary nail 101 such that removal of the second inlay 300 from the cannulation 120 is substantially prevented.

After the first inlay 200 and the second inlay 300 are inserted into the intramedullary nail 100, the cannulation 120 of the intramedullary nail 101, the cannulation 220 of the first inlay 200, and the cannulation 320 of the second inlay 300 form a cannulation (not labeled) that extends through the intramedullary nail assembly 100 from the trailing end 104 to the leading end 102.

The intramedullary nail assembly 100 is implanted by driving the assembly 100 into a medullary canal of a long bone such as a tibia, fibula, humerus, or femur. Prior to insertion of the assembly 100, a medical professional can enlarge the medullary canal to make room for the assembly 100. For example, the medullary canal can be enlarged by inserting a reaming rod down the medullary canal, and guiding a reamer head (not shown) with at least one cutting edge down the reaming rod such that the at least one cutting edge bores out the medullary canal. The reaming rod can be flexible so as to bend with the contour of the medullary canal. After enlarging the medullary canal, the intramedullary nail assembly 100 is then driven down into the enlarged medullary canal. In some cases, the reamer head can be removed, leaving the reaming rod in place, and the intramedullary nail assembly 100 can then be guided down the reaming rod into the medullary canal. As such, the reaming rod can be received in the cannulation 120 of the intramedullary nail 101, the cannulation 220 of the first inlay 200, and/or the cannulation 320 of the second inlay 300 as the nail assembly 100 is driven down the reaming rod into the medullary canal.

The intramedullary nail assembly 100 can be secured to the bone by (1) drilling, for each bone-anchor fixation hole 124 of the intramedullary nail aligned with a corresponding bone-anchor fixation hole 224 of the first inlay 200 and bone-anchor fixation hole 324 of the second inlay 300, a hole in the bone that aligns with the bone-anchor fixation hole, and (2) inserting, for each bone-anchor fixation hole, a bone anchor through the bone and into the respective bone-anchor fixation hole such that the bone anchor engages the bone on at least one side, such as opposed sides, of the intramedullary nail assembly 100. Angular stability as well as screw pull-out safety is provided to the intramedullary nail assembly 100 by the first and second inlays 200 and 300.

The intramedullary nail assembly 100 may be used in a variety of tools for inserting, setting, and aligning the assembly 100 within the bone. For example, targeting instruments, probes, locators, sensors, field generators, guide wires, removal hook instruments, or other tools/components may be used with the intramedullary nail assembly 100 for performing the medical procedure.

It will be appreciated that the foregoing description provides examples of the disclosed system and method. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

What is claimed is:

1. An intramedullary nail assembly, comprising:
an intramedullary nail having an outer surface and an opposing inner surface, the outer surface extending from a leading end of the intramedullary nail to a trailing end of the intramedullary nail, the inner surface defining a cannulation that extends into the trailing end towards the leading end about a central axis of the intramedullary nail, the intramedullary nail defining at least one nail hole that extends into the outer surface and through the inner surface; and an inlay having an outer surface and an opposing inner surface positionable within the cannulation, the inlay defining at least one inlay hole that extends into the outer surface of the inlay and through the inner surface of the inlay, the at least one nail hole being aligned with a respective at least one inlay hole when the inlay is positioned within the cannulation, the at least one nail hole having a cross-sectional dimension that is greater than a cross-sectional dimension of the respective at least one inlay hole, wherein the inlay includes at least one engagement feature that extends from the outer surface and is configured to engage the intramedullary nail when the inlay is inserted into the cannulation through the trailing end so as to limit both of (1) translation of the inlay relative to the intramedullary nail along the central axis of the intramedullary nail toward the trailing end and (2) rotation of the inlay relative to the intramedullary nail about the central axis, and wherein the at least one engagement feature includes an engagement member configured to engage the intramedullary nail to removably lock the inlay within the cannulation of the intramedullary nail, wherein the engagement member is configured flex inwardly toward a central axis of the intramedullary nail during insertion of the inlay into the cannulation.

2. The intramedullary nail assembly of claim 1, wherein the intramedullary nail includes a receiving element, the receiving element being configured to engage the engagement member of the inlay to removably lock the inlay within the cannulation of the body.

3. The intramedullary nail assembly of claim 1, wherein the engagement member is positioned adjacent to one of the at least one inlay hole.

4. The intramedullary nail assembly of claim 1, wherein the inlay is a first inlay, and wherein the at least one nail hole is a first at least one nail hole, the first inlay being positionable within the cannulation of a trailing body portion of the intramedullary nail that extends from the trailing end toward the leading end, the intramedullary nail further comprising:

a second inlay having an outer surface and an opposing inner surface positionable within the cannulation of a leading body portion of the intramedullary nail that extends from the leading end toward the trailing end, the second inlay defining a second at least one inlay hole that extends into the outer surface of the second inlay and through the inner surface of the second inlay, wherein a second at least one nail hole of the intramedullary nail us aligned with a respective second at least one inlay hole when the second inlay is positioned within the cannulation, the alignment of the second at least one nail hole and the second inlay hole defining another assembly hole that extends through the intramedullary nail assembly.

5. The intramedullary nail assembly of claim 4, wherein the engagement member is a first engagement member, wherein the second inlay includes a second engagement member configured to engage the intramedullary nail to removably lock the second inlay within the cannulation of the intramedullary nail.

6. The intramedullary nail assembly of claim 1, wherein the at least one nail hole and the at least one inlay hole comprise fastener holes, and wherein the at least one nail hole is substantially congruent to the at least one inlay hole.

7. The intramedullary nail assembly of claim 1, wherein the at least one nail hole and the at least one inlay hole comprise compression slots, and wherein the at least one nail hole is substantially congruent to the at least one inlay hole.

8. The intramedullary nail assembly of claim 1, wherein the inner surface of the intramedullary nail defines a nail shoulder, and wherein the outer surface of the inlay defines an inlay shoulder, wherein contact between the nail shoulder and the inlay shoulder when the inlay is positioned within the cannulation of the intramedullary nail substantially prevents movement of the inlay relative to the intramedullary nail in an axial direction.

9. An inlay for an intramedullary nail assembly, the intramedullary nail assembly including an intramedullary nail having an outer surface and an opposing inner surface, the outer surface extending from a leading end of the intramedullary nail to a trailing end of the intramedullary nail, the inner surface defining a cannulation that extends into the trailing end towards the leading end about a central axis of the intramedullary nail, and the intramedullary nail defining at least one nail hole that extends into the outer surface to the inner surface, the inlay comprising:

an outer surface and an opposing inner surface positionable within the cannulation, the inlay defining at least one inlay hole that extends into the outer surface of the inlay and through the inner surface of the inlay, the at least one inlay hole being aligned with a respective at least one nail hole when the inlay is positioned within the cannulation, the at least one inlay hole having a cross-sectional dimension that is smaller than a cross-sectional dimension of the respective at least one nail hole; and at least one engagement feature that extends from the outer surface and is configured to engage the intramedullary nail when the inlay is inserted into the cannulation through the trailing end so as to limit both of (1) translation of the inlay relative to the intramedullary nail along the central axis of the intramedullary nail toward the trailing end and (2) rotation of the inlay relative to the intramedullary nail about the central axis, wherein the inlay includes a leading body portion that defines a leading end of the inlay, and a trailing body portion that defines a trailing end of the inlay, the trailing body portion being offset from the leading body portion along a trailing direction, wherein a cross sectional dimension of the trailing body portion is different than a cross sectional dimension of the leading body portion such that an interface between the leading body portion and the trailing body portion defines an inlay shoulder.

10. The inlay of claim 9, wherein the at least one engagement feature includes an engagement member configured to engage the intramedullary nail to removably lock the inlay within the cannulation of the intramedullary nail.

11. The inlay of claim 9, wherein the inner surface of the inlay defining a cannulation, wherein when the inlay is positioned within the cannulation of the nail body a central axis of the cannulation of the inlay substantially aligns with a central axis of the cannulation of the intramedullary nail.

12. The inlay of claim 11, wherein the inlay defines a hole that extends into the outer surface of the inlay and through the inner surface of the inlay, the inlay hole being positioned to align with a hole defined by the intramedullary nail that extends into the outer surface of the intramedullary nail and through the inner surface of the intramedullary nail.

13. A method of assembling an intramedullary nail assembly, the method comprising:
aligning an inlay with an intramedullary nail, the intramedullary nail including a body having an outer surface and an opposing inner surface, the outer surface extending from a leading end of the body to a trailing end of the body, the inner surface defining a cannulation that extends into the trailing end towards the leading end about a central axis of the intramedullary nail, the intramedullary nail defining at least one nail hole that extends into the outer surface and through the inner surface; and
inserting the inlay into the cannulation of the body, the inlay having an outer surface and an opposing inner surface, the inlay defining at least one inlay hole that extends into the outer surface of the inlay and through the inner surface of the inlay, wherein after the inserting step, the at least one nail hole is aligned with a respective at least one inlay hole and an engagement feature that extends from the outer surface of the inlay engages the intramedullary nail so as to limit both of (1) translation of the inlay relative to the intramedullary nail along the central axis of the intramedullary nail toward the trailing end and (2) rotation of the inlay relative to the intramedullary nail about the central axis wherein the inserting step comprises causing the engagement member to flex inwardly toward a central axis of the intramedullary nail during insertion of the inlay into the cannulation.

14. The method of claim 13, wherein the inserting step comprises removably locking the inlay within the cannulation of the body after the inlay is inserted so as to limit linear and rotational movement between the inlay and the body.

15. The method of claim 13, wherein the inlay and an engagement member are a first inlay and a first engagement member, respectively, the first inlay being positioned within the cannulation of the trailing body portion, the method further comprising:
inserting a second inlay within the cannulation of the body within the leading body portion, the second inlay including a second engagement member configured to engage the body to removably lock the second inlay within the cannulation of the body after the second inlay is inserted.

* * * * *